United States Patent
Zhang

(10) Patent No.: US 8,712,521 B2
(45) Date of Patent: *Apr. 29, 2014

(54) METHOD AND APPARATUS FOR CONTROLLING CARDIAC RESYNCHRONIZATION THERAPY USING CARDIAC IMPEDANCE

(75) Inventor: Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/172,293

(22) Filed: Jun. 29, 2011

(65) Prior Publication Data

US 2011/0257547 A1 Oct. 20, 2011

Related U.S. Application Data

(63) Continuation of application No. 11/232,057, filed on Sep. 21, 2005, now Pat. No. 7,974,691.

(51) Int. Cl.
*A61N 1/368* (2006.01)

(52) U.S. Cl.
USPC .............................. 607/9; 600/509

(58) Field of Classification Search
USPC .............................. 607/9; 600/509
See application file for complete search history.

(56) References Cited

U.S. PATENT DOCUMENTS

| | | | |
|---|---|---|---|
| 5,179,946 A | 1/1993 | Weiss | |
| 5,188,106 A | 2/1993 | Nappholz et al. | |
| 5,235,976 A | 8/1993 | Spinelli | |
| 5,626,623 A | 5/1997 | Kieval et al. | |
| 5,788,643 A | 8/1998 | Feldman | |
| 5,800,467 A | 9/1998 | Park et al. | |
| 5,861,008 A | 1/1999 | Obel et al. | |
| 6,070,100 A | 5/2000 | Bakels et al. | |
| 6,076,015 A | 6/2000 | Hartley et al. | |
| 6,134,472 A | 10/2000 | Strandberg et al. | |
| 6,219,579 B1 | 4/2001 | Bakels et al. | |
| 6,223,079 B1 | 4/2001 | Bakels et al. | |
| 6,223,082 B1 | 4/2001 | Bakels et al. | |
| 6,238,420 B1 | 5/2001 | Bakels et al. | |
| 6,278,894 B1 | 8/2001 | Salo et al. | |
| 6,280,389 B1 | 8/2001 | Ding et al. | |
| 6,491,639 B1 | 12/2002 | Turcott | |
| 6,522,914 B1 | 2/2003 | Huvelle | |
| 6,556,866 B2 | 4/2003 | Dal Molin et al. | |
| 6,751,503 B1 | 6/2004 | Kroll | |
| 6,751,504 B2 | 6/2004 | Fishler | |
| 6,754,530 B2 | 6/2004 | Bakels et al. | |

(Continued)

OTHER PUBLICATIONS

U.S. Appl. No. 11/136,894, Examiner Interview Summary of Interview of Apr. 22, 2008, 1 pg.

(Continued)

*Primary Examiner* — Rex R Holmes
(74) *Attorney, Agent, or Firm* — Schwegman Lundberg & Woessner, P.A.

(57) ABSTRACT

This document discusses, among other things, systems, devices, and methods for measuring cardiac impedances and producing one or more resynchronization index parameters each indicative of a cardiac synchrony or asynchrony using the measured cardiac impedances. In one example, the one or more resynchronization index parameters are used to adjust one or more pacing parameters of a cardiac resynchronization therapy.

20 Claims, 19 Drawing Sheets

(56) References Cited

U.S. PATENT DOCUMENTS

| | | | |
|---|---|---|---|
| 6,876,881 B2 | 4/2005 | Baumann et al. | |
| 7,010,347 B2 | 3/2006 | Schecter | |
| 7,155,280 B2 | 12/2006 | Daum et al. | |
| 7,215,996 B2 | 5/2007 | Noren et al. | |
| 7,228,174 B2* | 6/2007 | Burnes et al. | 607/17 |
| 7,376,463 B2 | 5/2008 | Salo et al. | |
| 7,974,691 B2* | 7/2011 | Zhang | 607/9 |
| 2001/0010009 A1 | 7/2001 | Bakels et al. | |
| 2002/0002389 A1 | 1/2002 | Bradley et al. | |
| 2003/0100925 A1 | 5/2003 | Pape et al. | |
| 2003/0114889 A1 | 6/2003 | Huvelle et al. | |
| 2003/0216657 A1 | 11/2003 | Holmstrom et al. | |
| 2004/0015081 A1 | 1/2004 | Kramer et al. | |
| 2004/0015196 A1 | 1/2004 | Holmstrom et al. | |
| 2004/0049235 A1 | 3/2004 | Deno et al. | |
| 2004/0049238 A1 | 3/2004 | Jarverud | |
| 2004/0078058 A1 | 4/2004 | Holmstrom et al. | |
| 2004/0127944 A1 | 7/2004 | Casset | |
| 2004/0267142 A1 | 12/2004 | Paul | |
| 2005/0038481 A1 | 2/2005 | Chinchoy et al. | |
| 2005/0043895 A1 | 2/2005 | Schechter | |
| 2005/0049646 A1 | 3/2005 | Czygan et al. | |
| 2005/0085734 A1 | 4/2005 | Tehrani | |
| 2005/0102002 A1 | 5/2005 | Salo et al. | |
| 2005/0124901 A1 | 6/2005 | Misczynski et al. | |
| 2005/0182447 A1 | 8/2005 | Schecter | |
| 2005/0215914 A1 | 9/2005 | Bornzin et al. | |
| 2005/0216067 A1 | 9/2005 | Min et al. | |
| 2005/0277992 A1 | 12/2005 | Koh et al. | |
| 2005/0288725 A1 | 12/2005 | Hettrick et al. | |
| 2006/0020218 A1 | 1/2006 | Freeman et al. | |
| 2006/0247702 A1* | 11/2006 | Stegemann et al. | 607/17 |
| 2006/0271117 A1 | 11/2006 | Burnes et al. | |
| 2006/0271119 A1* | 11/2006 | Ni et al. | 607/9 |
| 2006/0271121 A1* | 11/2006 | Ding et al. | 607/17 |
| 2007/0043394 A1 | 2/2007 | Zhang et al. | |
| 2007/0100246 A1 | 5/2007 | Hyde | |
| 2007/0129639 A1 | 6/2007 | Zhang | |
| 2007/0149890 A1 | 6/2007 | Li et al. | |
| 2007/0191901 A1 | 8/2007 | Schecter | |
| 2007/0239044 A1 | 10/2007 | Ghanem et al. | |
| 2008/0058656 A1 | 3/2008 | Costello et al. | |
| 2008/0114410 A1* | 5/2008 | Ding et al. | 607/17 |

OTHER PUBLICATIONS

"U.S. Appl. No. 11/136,894, Final Office Action mailed Oct. 18, 2007", 9 pgs.

"U.S. Appl. No. 11/136,894, Non Final Office Action mailed Apr. 26, 2007", 8 pgs.

"U.S. Appl. No. 11/136,894, Response filed Feb. 22, 2007 to Restriction Requirement mailed Jan. 22, 2007", 18 pgs.

"U.S. Appl. No. 11/136,894, Response filed Jul. 26, 2007 to Non Final Office Action mailed Apr. 26, 2007", 15 pgs.

"U.S. Appl. No. 11/136,894, Restriction Requirement mailed Jan. 22, 2007", 5 pgs.

"U.S. Appl. No. 11/232,057, Appeal Brief filed Sep. 17, 2009", 29 pgs.

"U.S. Appl. No. 11/232,057, Examiner Interview Summary mailed Dec. 8, 2010", 3 pgs.

"U.S. Appl. No. 11/232,057, Examiner Interview Summary mailed Dec. 30, 2008", 4 pgs.

"U.S. Appl. No. 11/232,057, Final Office Action mailed Apr. 20, 2009", 9 pgs.

"U.S. Appl. No. 11/232,057, Non Final Office Action mailed Apr. 10, 2007", 8 pgs.

"U.S. Appl. No. 11/232,057, Non Final Office Action mailed Sep. 22, 2008", 6 pgs.

"U.S. Appl. No. 11/232,057, Non-Final Office Action mailed Sep. 1, 2010", 7 pgs.

"U.S. Appl. No. 11/232,057, Notice of Allowance mailed Feb. 28, 2011", 7 pgs.

"U.S. Appl. No. 11/232,057, Response filed Jan. 20, 2009 to Non Final Office Action mailed Sep. 22, 2008", 15 pgs.

"U.S. Appl. No. 11/232,057, Response filed Jul. 10, 2007 to Non Final Office Action mailed Apr. 10, 2007", 16 pgs.

"U.S. Appl. No. 11/232,057, Response filed Dec. 10, 2010 to Non Final Office Action mailed Sep. 1, 2010", 9 pgs.

"U.S. Appl. No. 11/232,057, Response filed Jun. 22, 2009 to Final Office Action mailed Apr. 20, 2009", 15 pgs.

"U.S. Appl. No. 11/232,057, Response filed Aug. 25, 2008 to Restriction Requirement mailed Jul. 25, 2008", 13 pgs.

"U.S. Appl. No. 11/232,057, Restriction Requirement mailed Jul. 25, 2008", 7 pgs.

"U.S. Appl. No. 12/016,830, Non Final Office Action mailed Jun. 8, 2011", 8 pgs.

"U.S. Appl. No. 12/016,830, Response filed Sep. 8, 2011 to Non Final Office Action mailed Jun. 8, 2011", 13 pgs.

"U.S. Appl. No. 12/016,830, Notice of Allowance mailed Oct. 19, 2011", 7 pgs.

U.S. Appl. No. 12/254,631, filed Oct. 20, 2008, Closed Loop Impedance-Based Cardiac Resynchronization Therapy Systems, Devices, and Methods.

U.S. Appl. No. 13/405,383, filed Feb. 27, 2012, Closed Loop Impedance-Based Cardiac Resynchronization Therapy Systems, Devices, and Methods.

"U.S. Appl. No. 13/405,383, Non Final Office Action mailed Apr. 11, 2013", 9 pgs.

"U.S. Appl. No. 13/405,383, Response filed Mar. 26, 2013 to Restriction Requirement mailed Feb. 27, 2013", 6 pgs.

"U.S. Appl. No. 13/405,383, Restriction Requirement mailed Feb. 27, 2013", 8 pgs.

\* cited by examiner

METHOD AND APPARATUS FOR CONTROLLING CARDIAC RESYNCHRONIZATION THERAPY USING CARDIAC IMPEDANCE

CLAIM OF PRIORITY

This application is a continuation of and claims the benefit of priority under 35 U.S.C. §120 to U.S. patent application Ser. No. 11/232,057, filed on Sep. 21, 2005, now issued as U.S. Pat. No. 7,974,691, which is hereby incorporated by reference herein in its entirety.

CROSS REFERENCE TO RELATED APPLICATIONS

This patent application is related to Jiang Ding et al. U.S. patent application Ser. No. 11/136,894, entitled "CLOSED LOOP IMPEDANCE-BASED CARDIAC RESYNCHRONIZATION THERAPY SYSTEMS, DEVICES, AND METHODS," filed on May 25, 2005, now abandoned, and Quan Ni et al. U.S. patent application Ser. No. 11/264,941, entitled "CLOSED LOOP IMPEDANCE-BASED CARDIAC RESYNCHRONIZATION THERAPY SYSTEMS, DEVICES, AND METHODS," filed on Nov. 2, 2005, now issued as U.S. Pat. No. 7,440,803, both assigned to Cardiac Pacemakers, Inc., which are incorporated by reference in their entirety.

TECHNICAL FIELD

This patent document pertains generally to cardiac function management devices, and more particularly, but not by way of limitation, to closed loop resynchronization therapy systems, devices, and methods.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. Some patients may have both irregular rhythms and poor spatial coordination of heart contractions. In either of these cases, diminished blood circulation may result. For such patients, a cardiac function management system may be used to improve the rhythm and/or spatial coordination of heart contractions. Such systems are often implanted in the patient and deliver therapy to the heart, such as electrical stimulation pulses that evoke or coordinate heart chamber contractions.

One problem faced by physicians treating cardiovascular patients is the treatment of congestive heart failure (also referred to as "CHF"). Congestive heart failure, which can result from a number of causes such as long-term hypertension, is a condition in which the muscle in the walls of at least one of the right and (more typically) the left side of the heart deteriorates. By way of example, suppose the muscle in the walls of left side of the heart deteriorates. As a result, the left atrium and left ventricle become enlarged, and that heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic electrical heart signals that control heart rhythm may also be affected. Normally, such intrinsic signals originate in the sinoatrial (SA) node in the upper right atrium, traveling through electrical pathways in the atria and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through specific electrical pathways in the ventricles and depolarizes the ventricular heart tissue such that resulting contractions of the right and left ventricles are triggered substantially simultaneously.

In the above example, where the left side of the heart has become enlarged due to congestive heart failure, however, the conduction system formed by the specific electrical pathways in the ventricle may be affected, as in the case of left bundle branch block (LBBB). As a result, ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in LBBB, for example, different regions within the left ventricle may not contract together in a coordinated fashion.

Cardiac function management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac function management systems also include cardiac resynchronization therapy (CRT) devices for coordinating the spatial nature of heart depolarizations for improving pumping efficiency, such as for patients having CHF. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together, such as to synchronize left and right side contractions.

Cardiac function management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac function management systems also include devices that combine these functions, as well as monitors, drug delivery devices, and any other implantable or external systems or devices for diagnosing or treating the heart.

The present inventors have recognized a need for improved techniques for determining the degree of asynchrony (also sometimes referred to as dyssynchrony) between the left and right sides of the heart of a CHF patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
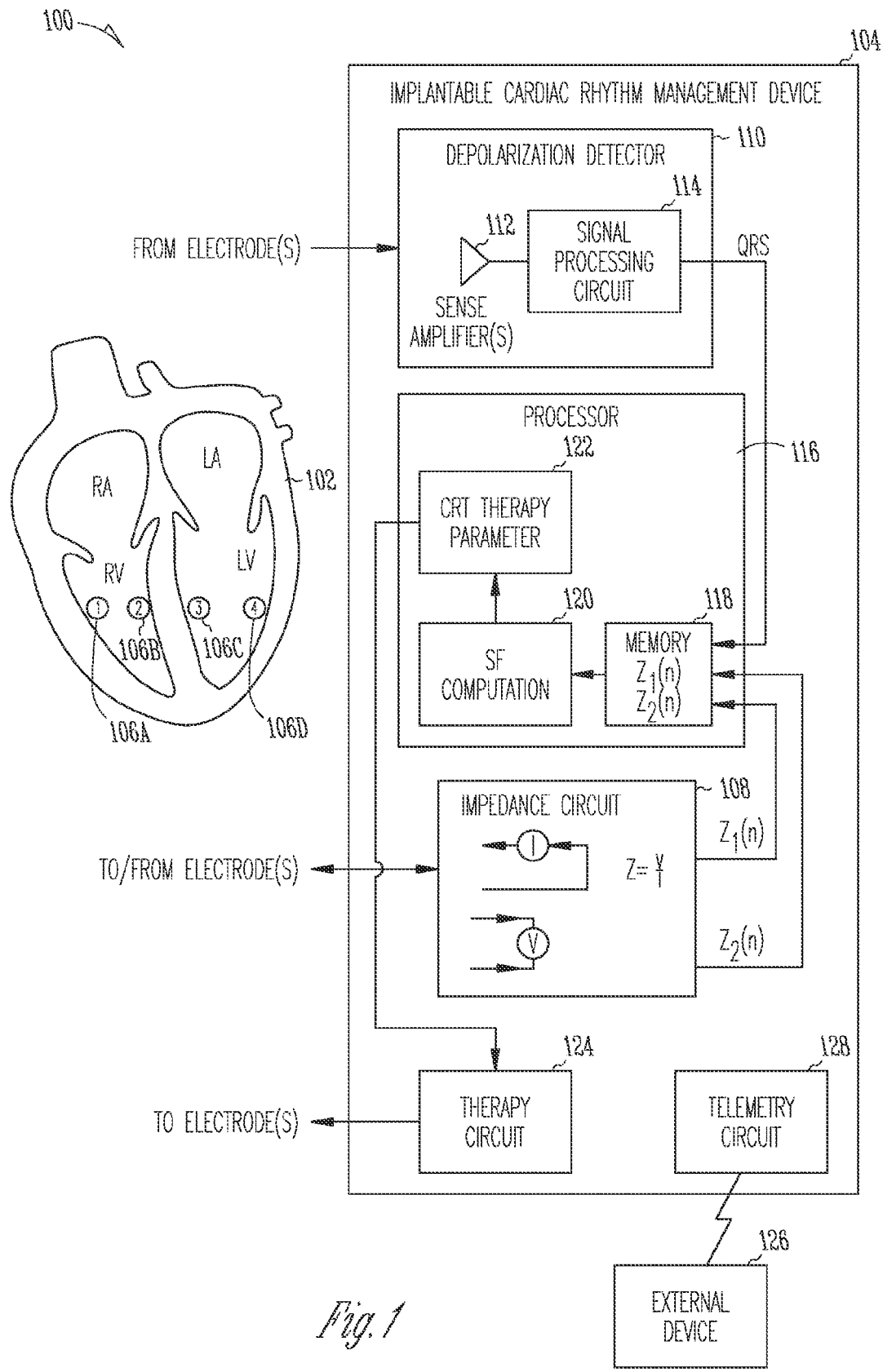
FIG. 1 is a schematic diagram illustrating generally one example of portions of a system and portions of an environment with which it is used.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present inventors have recognized a need for improved techniques for, among other things, determining the degree of asynchrony between the left and right sides of the heart of a CHF patient. For example, techniques that detect electrical depolarizations (e.g., QRS complexes) at the left and right sides of the heart to indicate the synchrony between the two sides of the heart are often not a good indicator of the actual mechanical synchrony between left and right ventricular heart contractions. Another technique, for example, use a pressure sensor to determine synchrony between left and right ventricular contractions. However, such a pressure-sensing technique typically requires a customized intracardiac lead that specially includes a pressure sensor. This adds expense and complexity to an implantable cardiac function management system.

This document describes, among other things, examples of cardiac function management systems, devices, and methods that measure an impedance, such as to determine or infer synchrony between right and left ventricles, or to provide another control parameter for adjusting cardiac resynchronization (CRT) therapy. In further examples, the impedance-derived information is used to automatically adjust one or more cardiac resynchronization therapy (CRT) parameters, such as on a beat-by-beat basis in a closed-loop feedback configuration, to provide improved spatial coordination of heart contractions (without necessarily affecting the actual heart rate of such heart contractions). The CRT therapy typically improves ventricular mechanical synchrony, stroke volume, coordination, etc. by manipulating the electrical activation sequence, such as by delivering appropriate stimulations to desired locations.

Example 1

FIG. 1 is a schematic diagram illustrating generally one example of portions of a system 100 and portions of an environment with which it is used, including a heart 102. In this example, the system 100 includes an implantable cardiac function management device 104. In one example, the device 104 is coupled to the heart 102 using one or more intravascular or other leadwires. The leadwires provide electrodes 106 in association with the heart 102. FIG. 1 illustrates an example that includes a first electrode 106A that is located at or near a right ventricular freewall, a second electrode 106B that is located at or near a right ventricular septum, a third electrode 106C that is located at or near a left ventricular septum, and a fourth electrode 106D that is located at or near a left ventricular freewall. This particular electrode configuration of FIG. 1 is useful for providing conceptual clarity, however, other possibly more practical electrode configurations will be discussed further below.

In FIG. 1, device 104 includes an impedance circuit 108 for measuring a first impedance indicative of right ventricular volume (e.g., between the first electrode 106A and the second electrode 106B) and a second impedance indicative of a left ventricular volume (e.g., between the third electrode 106C and the fourth electrode 106D). The first and second impedances are modulated as the right and left ventricles contract and expand. In one example, this impedance modulation is used to detect asynchrony between the left and right ventricular heart contractions, as discussed below.

In the example of FIG. 1, a depolarization detector circuit 110 detects intrinsic electrical heart depolarizations, such as by using one or more sense amplifiers 112 or signal processing circuits 114 to detect QRS complexes, which are depolarizations corresponding to ventricular heart contractions. The time interval between two successive QRS complexes can be used to define a cardiac cycle. In one example, the impedance modulation is monitored over a cardiac cycle for making the asynchrony determination, as discussed below.

In the example of FIG. 1, a microprocessor, microcontroller, or other processor circuit 116 executes, interprets, or otherwise performs instructions to provide computational ability. The impedance circuit 108 provides a sampled data right ventricular impedance waveform $Z_1(n)$ and a sampled data left ventricular impedance waveform $Z_2(n)$ to the processor 116 to be stored in a memory circuit 118 located within or external to the processor 116. In one example, the processor 116 uses a cardiac cycle's worth of the right ventricular impedance waveform $Z_1(n)$ and of the left ventricular impedance waveform $Z_2(n)$ to compute an indication of the degree of asynchrony (or, conversely, of synchrony) between the right and left ventricles, as discussed below. In one example, this indication is provided by a synchrony fraction (SF) computation module 120 comprising instructions that are executed by the processor 116. In a further example, the SF or other indication of asynchrony or synchrony is used to control at least one cardiac resynchronization therapy (CRT) parameter 122. The CRT parameter 122, in turn, controls one or more aspects of the delivery of stimulation pulses or other CRT therapy by therapy circuit 124, which is coupled to electrodes associated with the heart 102, such as electrodes 106 or other electrodes.

Impedance measurement circuit 108 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 106A-B, or the present electrodes 106C-D. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, they use an energy that avoids evoking a responsive heart contraction. These impedance testing parameters are also typically selected to avoid introducing a visible artifact on an ECG signal monitor of intrinsic heart signals.

The Hartley et al. U.S. Pat. No. 6,076,015 describes a suitable exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a suitable signal processing circuit for measuring a responsive voltage, such as between the present electrodes 106A-B, or between the present electrodes 106C-D. In one example, the signal processing circuit includes a preamplifier, demodulator, and bandpass filter for extracting the impedance data from the carrier signal, before conversion into digital form by an A/D converter. Further processing is performed digitally, and is typically performed differently in the present system 100 than in the Hartley et al. U.S. Pat. No. 6,076,015. For example, the present system typically includes a digital filter that passes frequency components of the measured impedance signal that are close to the frequency of heart contractions. The present digital filter typically attenuates other lower or higher frequency components of the measured impedance signal.

Figure 2:
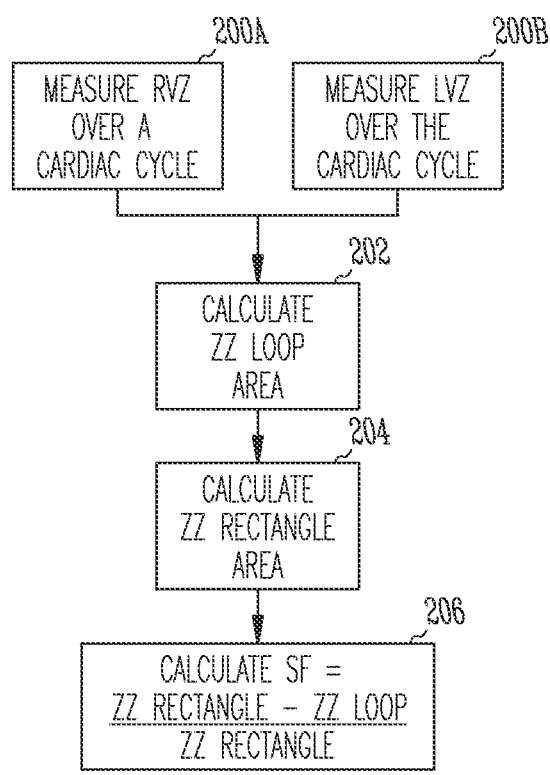
FIG. 2 is a flow chart illustrating generally one example of a technique for determining a degree of synchrony or asynchrony between left and right ventricular contractions of a heart.

FIG. 2 is a flow chart illustrating generally one example of a technique for determining a degree of synchrony or asynchrony between left and right ventricular contractions of a heart. At 200A, a right ventricular impedance ("RVZ" or "$Z_1$") is monitored over a cardiac cycle, such as by injecting a subthreshold (i.e., non-contraction-evoking) current and measuring a responsive voltage (e.g., using electrodes 106A-B). Concurrent with 200A, at 200B, a left ventricular impedance ("LVZ" or "$Z_2$") is monitored over the same cardiac cycle, such as by injecting a subthreshold current and measuring a responsive voltage (e.g., using electrodes 106C-D).

Figure 3A:
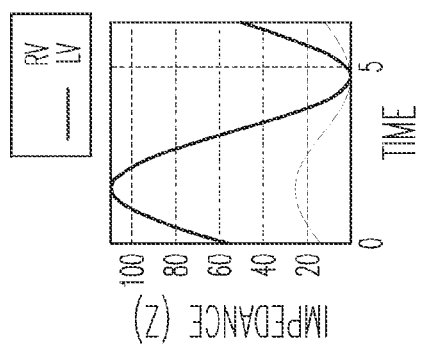
FIG. 3A is a conceptual (not real data) impedance vs. time graph of RVZ and LVZ over the same cardiac cycle for the case of synchrony between right and left ventricular contractions.
Figure 3B:
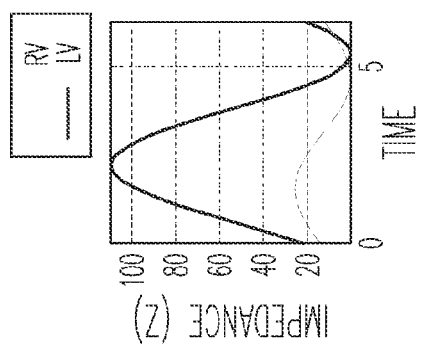
FIG. 3B is a conceptual (not real data) impedance vs. time graph of RVZ and LVZ over the same cardiac cycle for the case of mild asynchrony between right and left ventricular contractions.
Figure 3C:
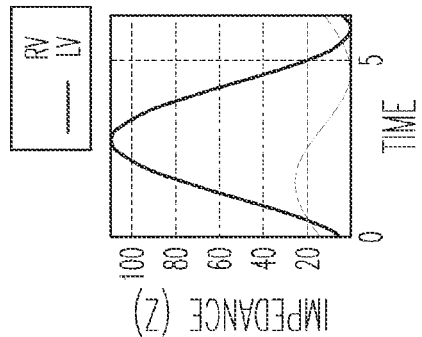
FIG. 3C is a conceptual (not real data) impedance vs. time graph of RVZ and LVZ over the same cardiac cycle for the case of severe asynchrony between right and left ventricular contractions.
Figure 4A:
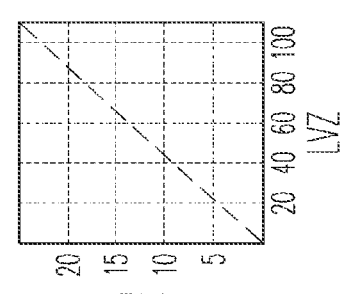
FIG. 4A is a graph (corresponding to FIG. 3A) of right ventricular impedance (RVZ) vs. left ventricular impedance (LVZ) for the case of synchrony between right and left ventricular contractions.
Figure 4B:
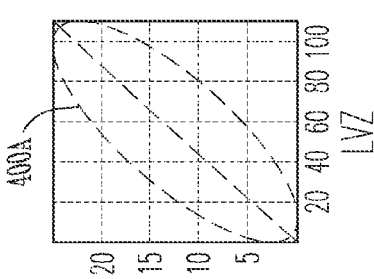
FIG. 4B is a graph (corresponding to FIG. 3B) of right ventricular impedance (RVZ) vs. left ventricular impedance (LVZ) for the case of mild asynchrony between right and left ventricular contractions.
Figure 4C:
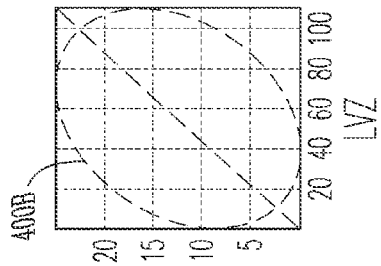
FIG. 4C is a graph (corresponding to FIG. 3C) of right ventricular impedance (RVZ) vs. left ventricular impedance (LVZ) for the case of severe asynchrony between right and left ventricular contractions.

FIGS. 3A, 3B, and 3C are conceptual (not real data) impedance vs. time graphs of RVZ and LVZ over the same cardiac cycle for the respective cases of synchrony, mild asynchrony, and severe asynchrony between right and left ventricular contractions. Corresponding to FIGS. 3A, 3B, and 3C, respectively, are the Lissajous graphs of FIGS. 4A, 4B, and 4C, which plot right ventricular impedance (RVZ) vs. left ventricular impedance (LVZ) for the respective cases of synchrony, mild asynchrony, and severe asynchrony between right and left ventricular contractions. As illustrated in FIGS. 4A, 4B, and 4C, as asynchrony increases, an interior loop area 400 swept by RVZ vs. LVZ over the cardiac cycle increases (e.g., from approximately zero in FIG. 4A for the case of synchrony).

At 202 in FIG. 2, the interior loop area 400 (as illustrated in FIG. 4) is calculated or approximated. A larger interior loop area indicates a larger degree of asynchrony. However, this value can be "normalized," if desired, such as described below with respect to 204 and 206. At 204, a ZZ Rectangle Area is calculated as ($LVZ_{maximum}$–$LVZ_{minimum}$)×($RVZ_{maximum}$–$RVZ_{minimum}$). $LVZ_{maximum}$ and $LVZ_{minimum}$ are the respective maximum and minimum values of LVZ during the cardiac cycle. $RVZ_{maximum}$–$RVZ_{minimum}$ are the respective maximum and minimum values of RVZ during the same cardiac cycle.

At 206, a synchrony fraction (SF) is computed as (ZZ Rectangle Area−ZZ Loop Area)÷(ZZ Rectangle Area). SF provides an indication of synchrony between right and left ventricular contractions. In theory, complete asynchrony is indicated by SF=0 and perfect synchrony is indicated by SF=1. For example, FIG. 4A illustrates SF=1, FIG. 4B illustrates SF=0.5, and FIG. 4C illustrates SF=0.2. Thus, SF provides an intuitive measure of mechanical synchrony, similar to using the commonly known ejection fraction (EF) measure of cardiac pumping function. Alternatively, an asynchrony fraction (ASF) could be computed as (1−SF). Because of the above "normalization," the SF is independent of absolute measurements of intracardiac impedance and, therefore, should not require any patient-specific calibration.

In one example, the SF, ASF, or other indication of synchrony or asynchrony is used in a closed loop system to adjust the value of one or more CRT parameters to increase SF or decrease ASF. Examples of CRT parameters that can be varied to improve synchrony include, among other things: particular cardiac electrode site(s), atrioventricular (AV) delay, interventricular delay, or intraventricular delay.

In another example, the SF, ASF, or other indication of synchrony or asynchrony is communicated from the implantable device 104 to a local or remote external device 126, such as by using a telemetry circuit 128 included within the implantable device 104. The indication can be displayed to physician or other caregiver, such as on a computer monitor portion of the external device 126.

In another example, the SF, ASF, or other indication of synchrony or asynchrony triggers a warning when the degree of asynchrony exceeds a particular threshold value. In one example, the warning is communicated to the external device 126, as described above. In another example, the warning is communicated directly to the patient, such as by providing an audible, vibrating, or other warning indicator within the implantable device 104.

Figure 5A:
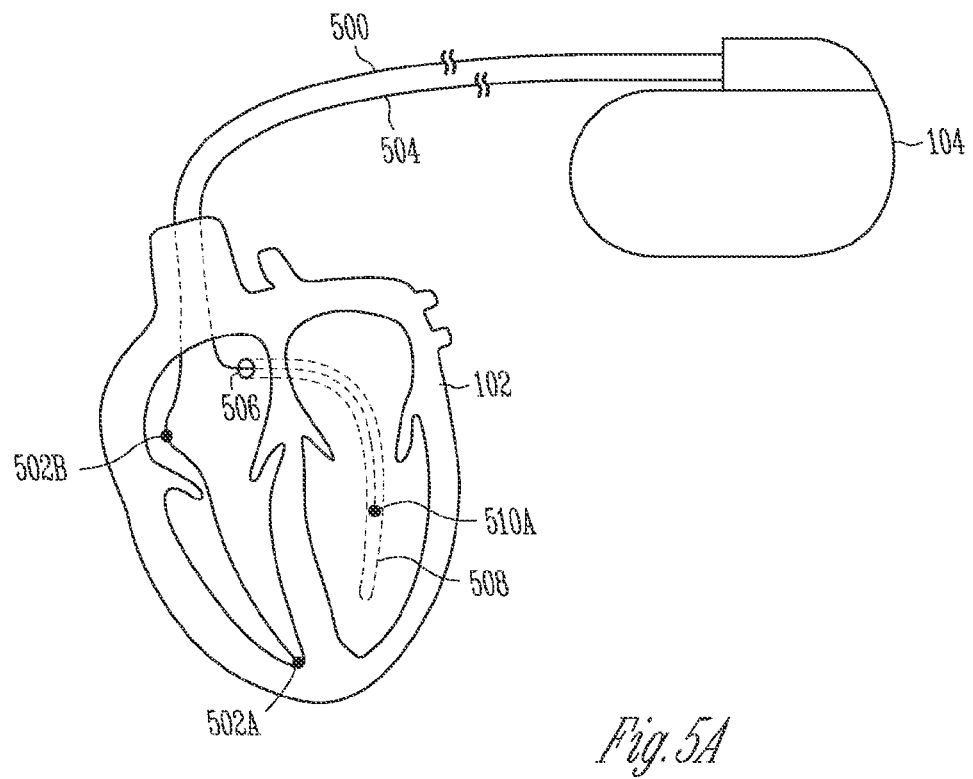
FIG. 5A is a schematic illustration of another useful electrode configuration that can be used in conjunction with the techniques described above with respect to FIGS. 1 and 2.
Figure 5B:
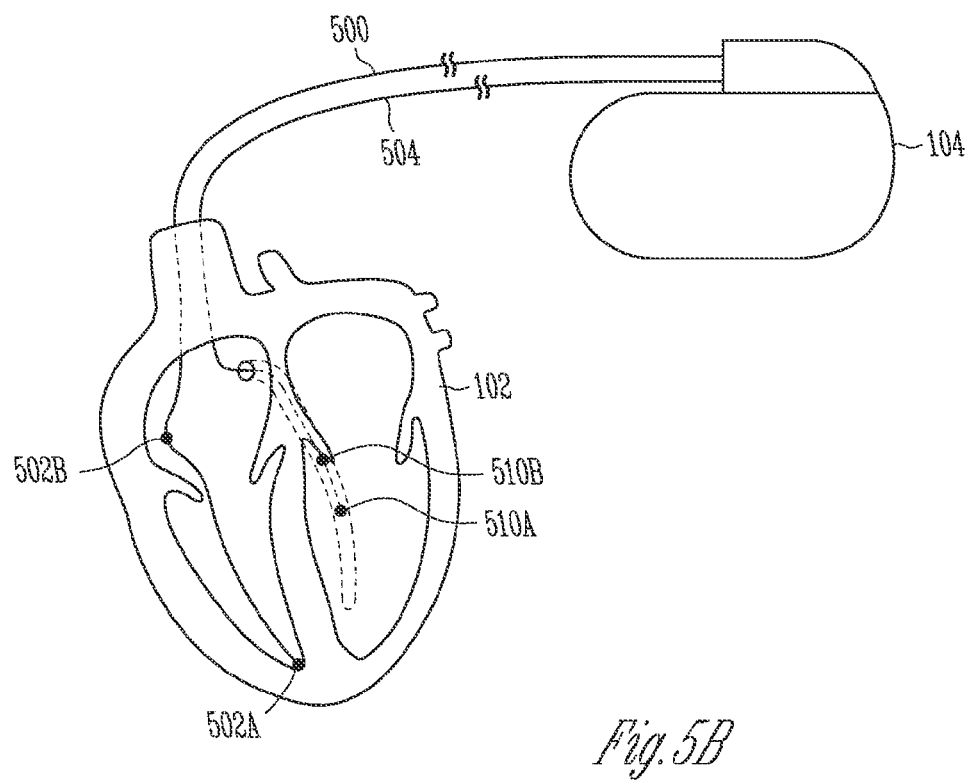
FIG. 5B is a schematic illustration of yet another useful electrode configuration that can be used in conjunction with the techniques described above with respect to FIGS. 1 and 2.

FIG. 1 illustrated an example of an electrode configuration that is particularly useful for conceptualizing how impedance can be correlated to right and left ventricular volumes. However, other electrode configurations can also be used in conjunction with the techniques described above with respect to FIGS. 1 and 2. In one such electrode configuration, the electrodes 106B and 106C are merged into a common septal electrode. FIGS. 5A and 5B are schematic illustrations of some other useful electrode configurations that can be used in conjunction with the techniques described above with respect to FIGS. 1 and 2.

In FIG. 5A, the implantable device 104 is coupled to the heart 102 using a first lead 500 that includes a right ventricular electrode 502A located at or near the right ventricular apex. The lead 500 (or, alternatively, a separate right atrial lead) also includes a right atrial electrode 502B. In FIG. 5A, the implantable device 104 is also coupled to the heart 102 using a second lead 504 that extends into the coronary sinus 506 and into a coronary sinus vein 508 such that its distal electrode 510A is located in the coronary sinus vein 508 in association with the left ventricular freewall. The example of FIG. 5A approximates right ventricular volume using a right ventricular impedance (RVZ) obtained between the right atrial electrode 502B and the right ventricular electrode 502A. The example of FIG. 5A approximates left ventricular volume using a left ventricular impedance (LVZ) obtained between right atrial electrode 502B and left ventricular electrode 510A. This electrode configuration is practical because it potentially makes use of existing electrodes available with existing leads, however, it may be confounded slightly by other effects, such as right atrial volume fluctuations arising from right atrial contractions.

FIG. 5B is similar to FIG. 5A, however, FIG. 5B includes an additional electrode 510B on the coronary sinus lead 504. The electrode 510B is located in the mid coronary sinus at a location that is closer to the left atrium. The example of FIG. 5B approximates right ventricular volume using a right ventricular impedance (RVZ) obtained between the right atrial electrode 502B and the right ventricular electrode 502A. The example of FIG. 5B approximates left ventricular volume using a left ventricular impedance (LVZ) obtained between left atrial electrode 510B and left ventricular electrode 510A. This electrode configuration is practical because it potentially makes use of existing electrodes available with existing leads, however, it may be confounded slightly by other effects, such as right atrial volume fluctuations arising from right atrial contractions. However, this electrode configuration provides a global indication of left and right side synchrony or asynchrony, including atrial effects.

The example described above with respect to FIGS. 1-5B increases the SF by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may increase the SF at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Example 2

Figure 6:
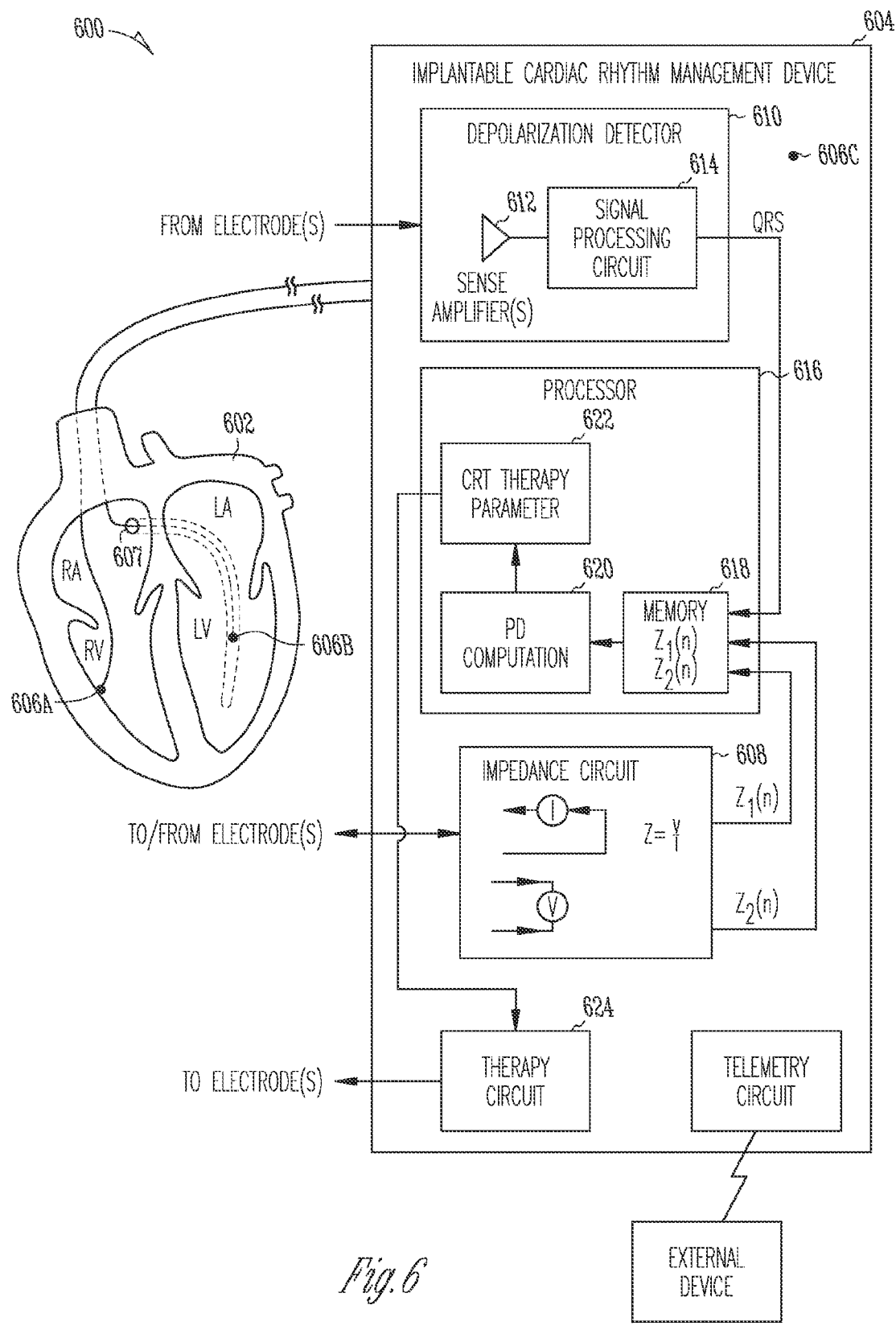
FIG. 6 is a schematic diagram illustrating generally one example of portions of a system and portions of an environment with which it is used.

FIG. 6 is a schematic diagram illustrating generally one example of portions of a system 600 and portions of an environment with which it is used, including a heart 602. In this example, the system 600 includes an implantable cardiac function management device 604. In one example, the device 604 is coupled to the heart 602 using one or more intravascular or other leads. The leads provide electrodes 606 in association with the heart 602. FIG. 6 illustrates an example that includes a first electrode 606A that is located at or near an midportion of a right ventricular freewall, a second electrode 606B that is located in association with a left ventricular freewall, such as by being introduced on an intravascular lead that is inserted into coronary sinus 607 toward a coronary sinus vein. A third electrode 606C is located on a hermetically-sealed housing ("can") of the implantable device 604 (or, alternatively, on an insulating "header" extending from the housing of the implantable device 604).

In FIG. 6, the device 604 includes an impedance circuit 608 for measuring a right ventricular impedance between the first electrode 606A and the third electrode 606C and a left ventricular impedance between the second electrode 606B and the third electrode 606C. The right and left ventricular impedances are modulated as the right and left ventricles contract and expand. In one example, this impedance modulation is used to detect asynchrony between the left and right ventricular heart contractions, as discussed below.

In the example of FIG. 6, a depolarization detector circuit 610 detects intrinsic electrical heart depolarizations, such as by using one or more sense amplifiers 612 or signal processing circuits 614 to detect QRS complexes, which are depolarizations corresponding to ventricular heart contractions. The time interval between two successive QRS complexes can be used to define a cardiac cycle. In one example, the impedance modulation is monitored over all or a particular desired portion of a cardiac cycle for making the asynchrony determination, as discussed below.

In the example of FIG. 6, a microprocessor, microcontroller, or other processor circuit 616 executes instructions to provide computational ability. The impedance circuit 608 provides a sampled data right ventricular impedance waveform $Z_1(n)$ and a sampled data left ventricular impedance waveform $Z_2(n)$ to the processor 616 to be stored in a memory circuit 618 located within or external to the processor 616. In one example, the processor 616 samples at least a portion of a cardiac cycle's worth of the right ventricular impedance waveform $Z_1(n)$ and of the left ventricular impedance waveform $Z_2(n)$ to compute an indication of the degree of asynchrony (or, conversely, of synchrony) between the right and left ventricles, as discussed below. In one example, this indication is provided by a phase difference (PD) computation module 620 comprising instructions that are executed by the processor 616. In a further example, the PD or other indication of asynchrony or synchrony is used to control at least one cardiac resynchronization therapy (CRT) parameter 622. The CRT parameter 622, in turn, controls one or more aspects of the delivery of stimulation pulses or other CRT therapy by therapy circuit 624, which is coupled to electrodes associated with the heart 602, such as electrodes 606 or other electrodes.

Impedance measurement circuit 608 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 606A and 606C, or the present electrodes 606B and 606C. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 606A and 606C, or between the present electrodes 606B and 606C. In one example, the signal processing circuit includes a preamplifier, demodulator, and bandpass filter for extracting the impedance data from the carrier signal, before conversion into digital form by an A/D converter. Further processing is performed digitally, and is performed differently in the present system 600 than in the Hartley et al. U.S. Pat. No. 6,076,015. The impedance circuit 608 of the present system typically includes a digital filter that passes frequency components of the measured impedance signal that are close to the frequency of heart contractions. The digital filter typically attenuates other lower or higher frequency components of the measured impedance signal.

Figure 7:
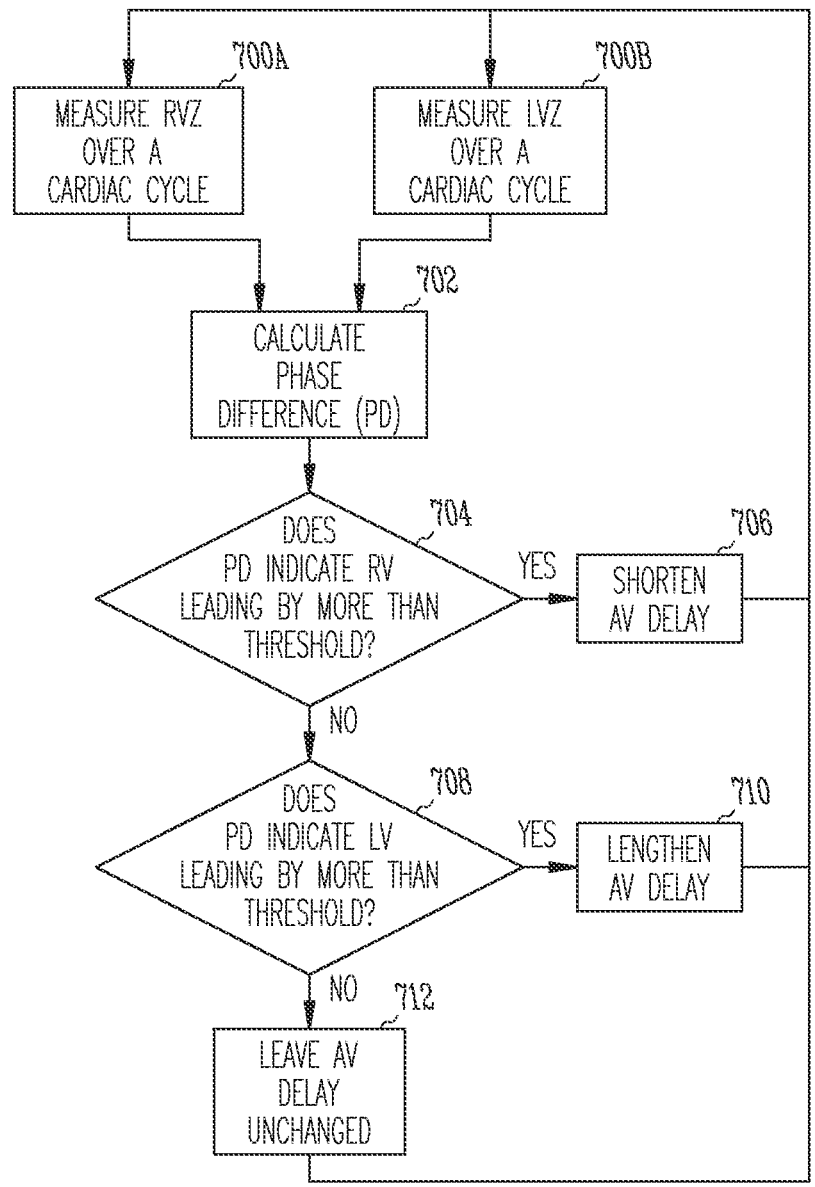
FIG. 7 is a flow chart illustrating generally one example of a technique for determining a degree of synchrony or asynchrony between left and right ventricular contractions of a heart.

FIG. 7 is a flow chart illustrating generally one example of a technique for determining a degree of synchrony or asynchrony between left and right ventricular contractions of a heart. At 700A, a right ventricular impedance (RVZ) is monitored over a cardiac cycle, such as by injecting a subthreshold (i.e., non-contraction-evoking) current (e.g., between electrodes 606A and 606C) and measuring a responsive voltage (e.g., using electrodes 606A and 606C). Concurrent with 700A, at 700B, a left ventricular impedance (LVZ) is monitored over the same cardiac cycle, such as by injecting a subthreshold current (e.g., between electrodes 606B and 606C) and measuring a responsive voltage (e.g., using electrodes 606B and 606C).

At 702, a phase difference (PD) between the right and left ventricular contractions is calculated using the RVZ and LVZ. In one embodiment, the phase difference is calculated by measuring a time difference between the same artifact on each of the RVZ and LVZ signals. In one example, a zero-cross detector detects a like zero-crossing artifact in each of the RVZ and LVZ signals, and PD is then calculated as the time difference between occurrences of these two like zero-crossings. In another example, a peak-detector detects a like peak artifact in each of the RVZ and LVZ signals, and PD is then calculated as the time difference between occurrences of these two like peaks. In yet another example, a level-detector detects a like level in each of the RVZ and LVZ signals, and PD is then calculated as a time difference between the occurrences of these two like signal levels.

Figure 8:
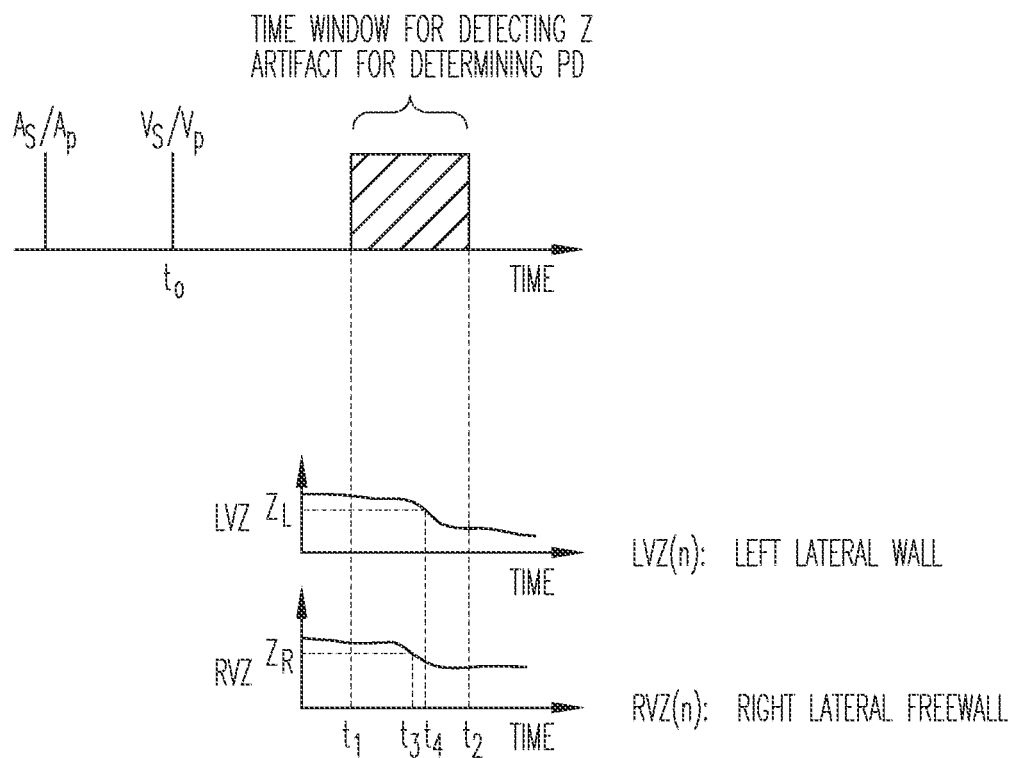
FIG. 8 is a conceptualized (not real data) signal diagram illustrating an embodiment in which a time window is established for identifying an impedance artifact.

In one embodiment, in order to better identify a like impedance artifact in each of the RVZ and LVZ signals for obtaining the phase difference, the zero-crossing, peak-detect, level-detect, etc. is performed during a particular time window portion of the cardiac cycle. In one example, this is accomplished by establishing such a time window relative to a QRS complex or other electrical artifact as detected by the depolarization detector 610, as illustrated in the conceptualized (not real data) signal diagram of FIG. 8. In FIG. 8, a time window between $t_1$ and $t_2$ is triggered following predetermined delay from a ventricular sense ($V_S$) QRS complex or ventricular pace at time $t_0$. During the time window, the LVZ and RVZ are examined for the occurrence of a particular impedance artifact. In the illustrated conceptual example, the impedance artifact is an LVZ falling below a certain threshold value $Z_L$ (which occurs, in this example, at time $t_4$) and a corresponding RVZ falling below a corresponding threshold value $Z_R$ (which occurs, in this example, at time $t_3$). In this example, the PD magnitude is $t_4-t_3$ with RVZ leading.

In FIG. 7, at 704 if PD indicates that the right ventricle is leading by more than a threshold value (PDT+), then at 706, the AV delay is shortened by a small incremental value, which tends to reduce the amount by which the right ventricle leads the left ventricle. Otherwise, at 708, if the PD indicates that the left ventricle is leading by more than a threshold value (PDT−), then at 710, the AV delay is lengthened by a small incremental value, which tends to reduce the amount by which the left ventricle leads the right ventricle. Otherwise, at 712, if neither the right or left ventricles is leading by more than its respective threshold, then the AV delay is left unchanged, which tends to leave the synchrony between the left and right ventricles unchanged. The behavior of 704-712 is further understood by reference to the phase delay vs. AV delay graph of FIG. 9. Using PD as an error signal in a closed loop system to control a CRT parameter (such as AV Delay), FIG. 9 illustrates how synchrony between the left and right ventricles is promoted.

Figure 9:
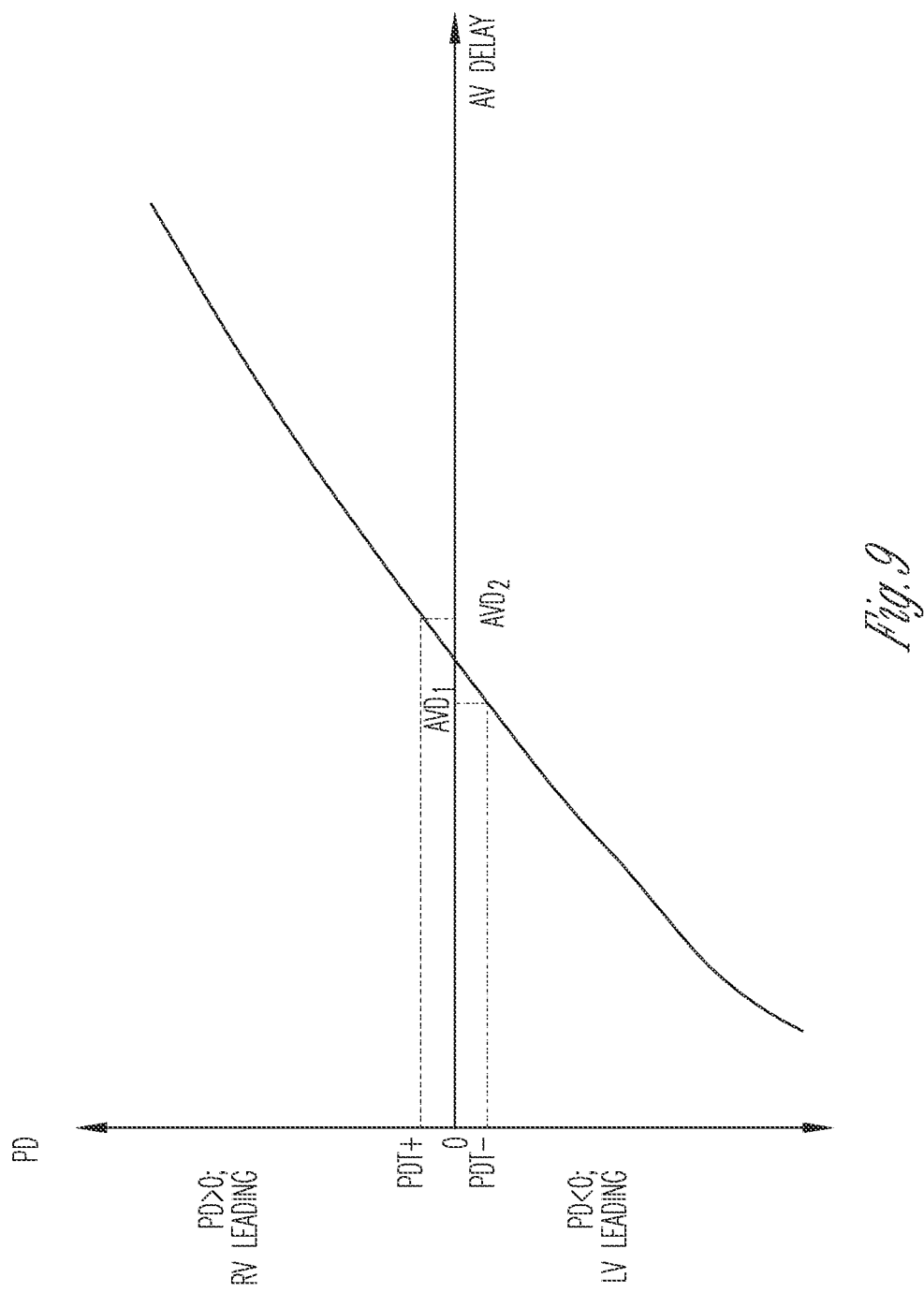
FIG. 9 is a graph of phase delay vs. AV delay.

Although FIGS. 7 and 9 illustrate AV delay as the particular CRT parameter being modified to effect closed-loop control reducing PD, other CRT parameters could similarly be modified to reduce PD. Another example of a CRT parameter is LV offset (LVO), which is the difference between a right ventricular AV delay (AVDR) and a left ventricular AV delay (AVDL). More particularly, LVO=AVDL−AVDR. Therefore, a positive LVO indicates that the right ventricle is programmed to be stimulated earlier than the left ventricle; a negative LVO indicates that the left ventricle is programmed to be stimulated earlier than the right ventricle. In one example, the LVO is adjusted in a closed-loop fashion to reduce the PD error signal, in a similar manner to that illustrated in FIGS. 7 and 9. Similarly, other CRT parameter(s) can be adjusted in a closed-loop fashion to reduce the PD error signal and improve right and left ventricular mechanical synchrony.

The example described above with respect to FIGS. 6-9 reduces the PD by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may reduce the PD at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Example 3

Figure 10:
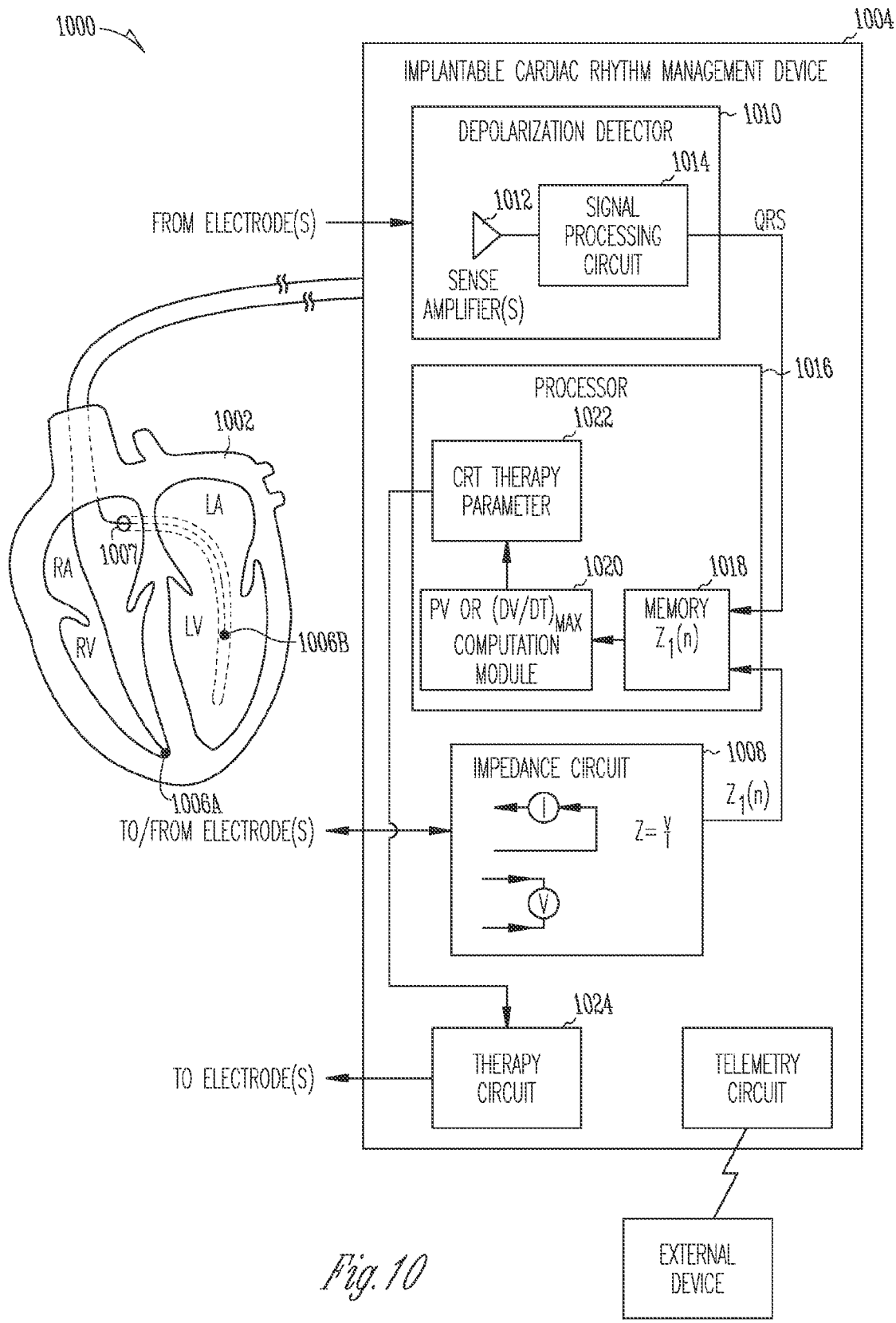
FIG. 10 is a schematic diagram illustrating generally one example of portions of a system and portions of an environment with which it is used.

FIG. 10 is a schematic diagram illustrating generally one example of portions of a system 1000 and portions of an environment with which it is used, including a heart 1002. In this example, the system 1000 includes an implantable cardiac function management device 1004. In one example, the device 1004 is coupled to the heart 1002 using one or more intravascular or other leads. The leads provide electrodes 1006 in association with the heart 1002. FIG. 10 illustrates an example that includes a first electrode 1006A that is located at or near a middle or apical portion of a right ventricular septum, a second electrode 1006B that is located in association with a left ventricular freewall, such as by being introduced on an intravascular lead that is inserted into coronary sinus 1007 toward a lateral or posterior coronary sinus vein.

In FIG. 10, the device 1004 includes an impedance circuit 1008 for measuring a left ventricular impedance between the first electrode 1006A and the second electrode 1006B. The left ventricular impedance is modulated as the left ventricle contracts and expands. In one example, this impedance modulation is used to control a cardiac resynchronization therapy (CRT) parameter, as discussed below.

In the example of FIG. 10, a depolarization detector circuit 1010 detects intrinsic electrical heart depolarizations, such as by using one or more sense amplifiers 1012 or signal processing circuits 1014 to detect QRS complexes, which are depolarizations corresponding to ventricular heart contractions. The time interval between two successive QRS complexes can be used to define a cardiac cycle. In one example, the impedance modulation is monitored over all or a particular desired portion of a cardiac cycle for making the asynchrony determination, as discussed below.

In the example of FIG. 10, a microprocessor, microcontroller, or other processor circuit 1016 executes instructions to provide computational ability. The impedance circuit 1008 provides a sampled data ventricular impedance waveform $Z_1(n)$ to the processor 1016 to be stored in a memory circuit 1018 located within or external to the processor 1016. In this illustrative example, the sampled data ventricular impedance waveform $Z_1(n)$ is a left ventricular impedance. However, it is understood that this technique could alternatively be implemented using a right ventricular impedance waveform $Z_1(n)$.

In one example, the processor 1016 samples a cardiac cycle's worth of the left ventricular impedance waveform $Z_1(n)$ to compute one or both of: (1) an impedance-indicated peak-to-peak volume (PV) indication of the left ventricle; or (2) an impedance-indicated maximum rate of change in left ventricular volume ($(dV/dt)_{max}$), as discussed below. In one example, the PV or $(dV/dt)_{max}$ is provided by a peak volume (PV) or $(dV/dt)_{max}$ computation module 1020 comprising instructions that are executed by the processor 1016. In a further example, the PV or $(dV/dt)_{max}$ is used to control at least one cardiac resynchronization therapy (CRT) parameter 1022 such that it tends to increase PV or $(dV/dt)_{max}$. The CRT parameter 1022, in turn, controls one or more aspects of the delivery of stimulation pulses or other CRT therapy by therapy circuit 1024, which is coupled to electrodes associated with the heart 1002, such as electrodes 1006 or other electrodes.

Impedance measurement circuit 1008 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 1006A and 1006B. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 1006A and 1006B. In one example, the signal processing circuit includes a preamplifier, demodulator, and bandpass filter for extracting the impedance data from the carrier signal, before conversion into digital form by an A/D converter. Further processing is performed digitally, and is performed differently in the present system 1000 than in the Hartley et al. U.S. Pat. No. 6,076,015. The impedance circuit 1008 of the present system typically includes a digital filter that passes frequency components of the measured impedance signal that are close to the frequency of heart contractions. The digital filter typically attenuates other lower or higher frequency components of the measured impedance signal.

Figure 11:
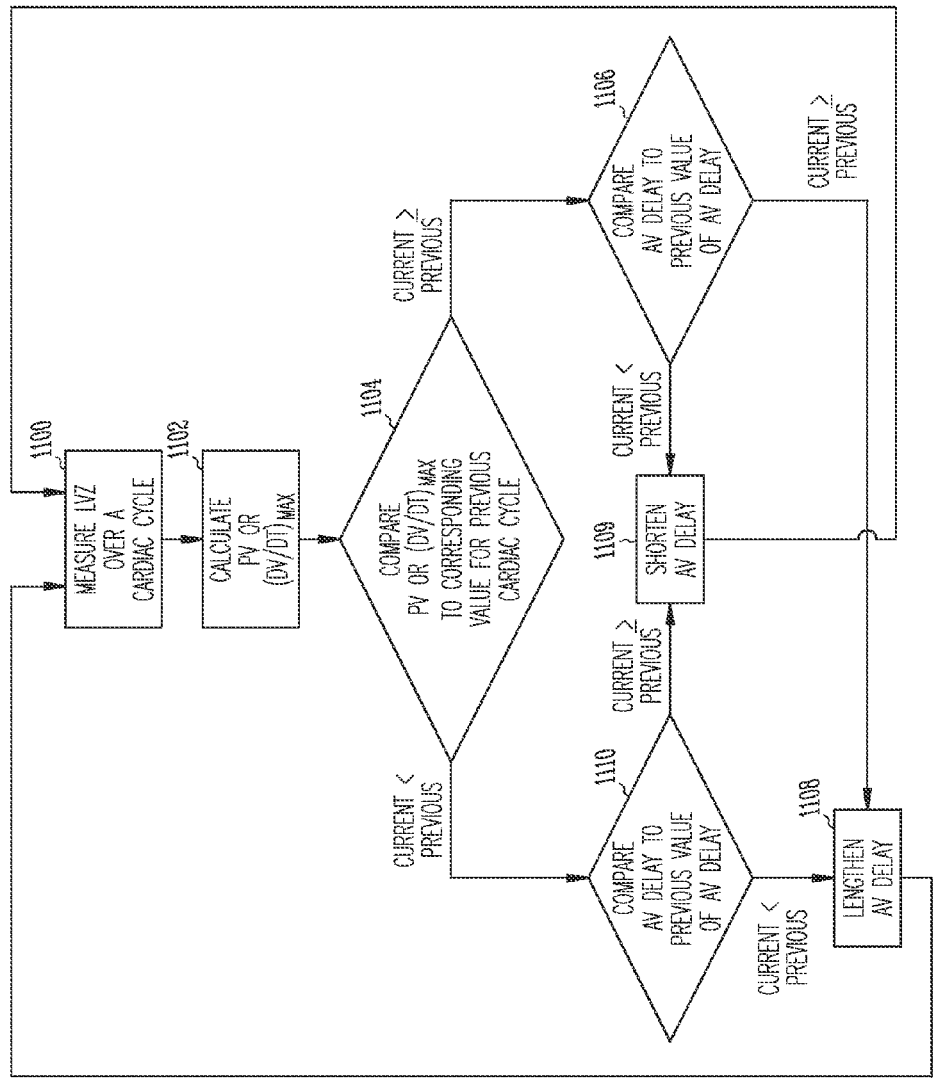
FIG. 11 is a flow chart illustrating generally one example of a technique for controlling a cardiac resynchronization therapy (CRT) parameter in a way that tends to increase an impedance-based indication of peak-to-peak volume (PV) or $(dV/dt)_{max}$.

FIG. 11 is a flow chart illustrating generally one example of a technique for controlling a cardiac resynchronization therapy (CRT) parameter in a way that tends to increase an impedance-based indication of PV or $(dV/dt)_{max}$. At 1100, a left ventricular impedance (LVZ) is monitored over a cardiac cycle, such as by injecting a subthreshold (i.e., non-contraction-evoking) current (e.g., between electrodes 1006A-B) and measuring a responsive voltage (e.g., using electrodes 1006A-B).

At 1102, a peak-to-peak volume (PV) or $(dV/dt)_{max}$ is calculated using the LVZ signal. At 1104 one of the (PV) or $(dV/dt)_{max}$ is compared to its corresponding value for the previous cardiac cycle. If the current value equals or exceeds the previous value, then at 1106 the current AV delay is compared to an AV delay from the previous cardiac cycle (or an averaged or filtered value over several such prior cardiac cycles). If, at 1106, the current AV delay equals or exceeds the previous AV delay, then at 1108, the AV delay is lengthened slightly for the next cardiac cycle and process flow returns to 1100. Otherwise, at 1106, if the current AV delay is less than the previous AV delay, then the AV delay is shortened slightly at 1109 for the next cardiac cycle and process flow returns to 1100.

At 1104, if the current value is less than the previous value, then at 1110. The current AV delay is compared to an AV delay from the previous cardiac cycle (or an averaged or filtered value over several such prior cardiac cycles). If, at 1110, the current AV delay equals or exceeds the previous AV delay, then the AV delay is shortened slightly for the next cardiac cycle at 1109 and process flow returns to 1100. Otherwise, at 1110, if the current AV delay is less than the previous AV delay, then at 1108 the AV delay is lengthened slightly for the next cardiac cycle and process flow returns to 1100.

Figure 12A:
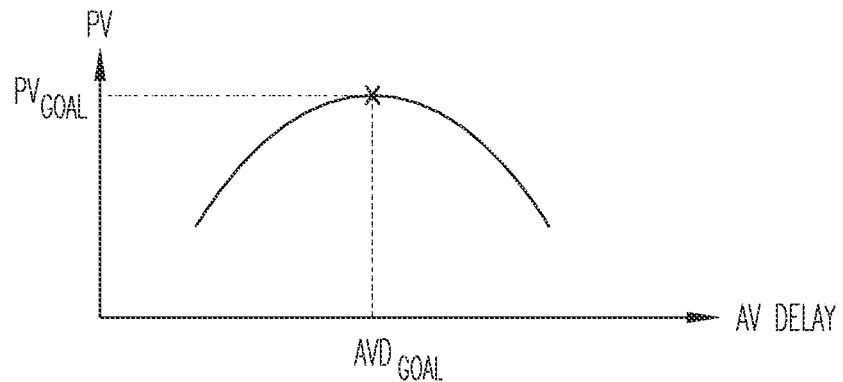
FIG. 12A is a graph of peak-to-peak volume (PV) vs. AV Delay.
Figure 12B:
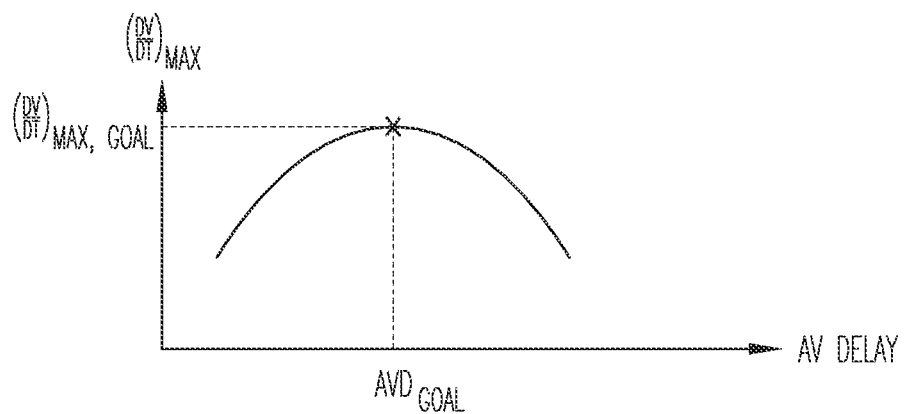
FIG. 12B is a graph of $(dV/dt)_{max}$ vs. AV Delay.

Thus, in the example of FIG. 11, a CRT parameter such as AV delay is adjusted in such a way that it tends to increase PV or $(dV/dt)_{max}$, as illustrated conceptually in the graphs of FIGS. 12A and 12B. In another embodiment, the CRT parameter is adjusted in such a way that it tends to increase a weighted measure of both PV and $(dV/dt)_{max}$. Similarly, other CRT parameter(s) can be adjusted in a closed-loop fashion to increase PV or $(dV/dt)_{max}$. In FIG. 11, each condition (current=previous) can alternatively be associated with (current<previous), instead of being associated with (current>previous), as indicated in the example of FIG. 11.

Figure 13:
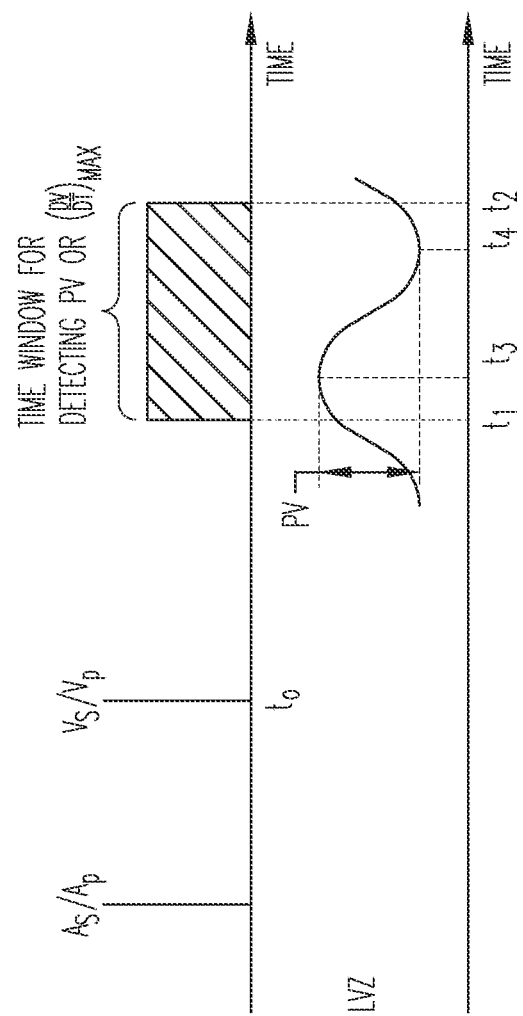
FIG. 13 is a conceptualized (not real data) signal diagram illustrating an embodiment in which a time window is established for measuring the peak-to-peak volume (PV) or $(dV/dt)_{max}$.

In one embodiment, in order to better identify the desired control parameter(s) PV or $(dV/dt)_{max}$, the peak-to-peak or slope measurement is performed during a particular time window portion of the cardiac cycle. In one example, this is accomplished by establishing such a time window relative to a QRS complex or other electrical artifact as detected by the depolarization detector 1010, as illustrated in the conceptualized (not real data) signal diagram of FIG. 13. In FIG. 13, a time window between $t_1$ and $t_2$ is triggered following predetermined delay from a ventricular sense ($V_S$) QRS complex or ventricular pace ($V_P$) at time $t_0$. During the time window, the LVZ limits the time period for measuring the control parameter PV or $(dV/dt)_{max}$. In the illustrated conceptual example, the PV is measured between times $t_3$ and $t_4$, which correspond to maximum and minimum values of the LVZ, respectively.

Example 4

Figure 14:
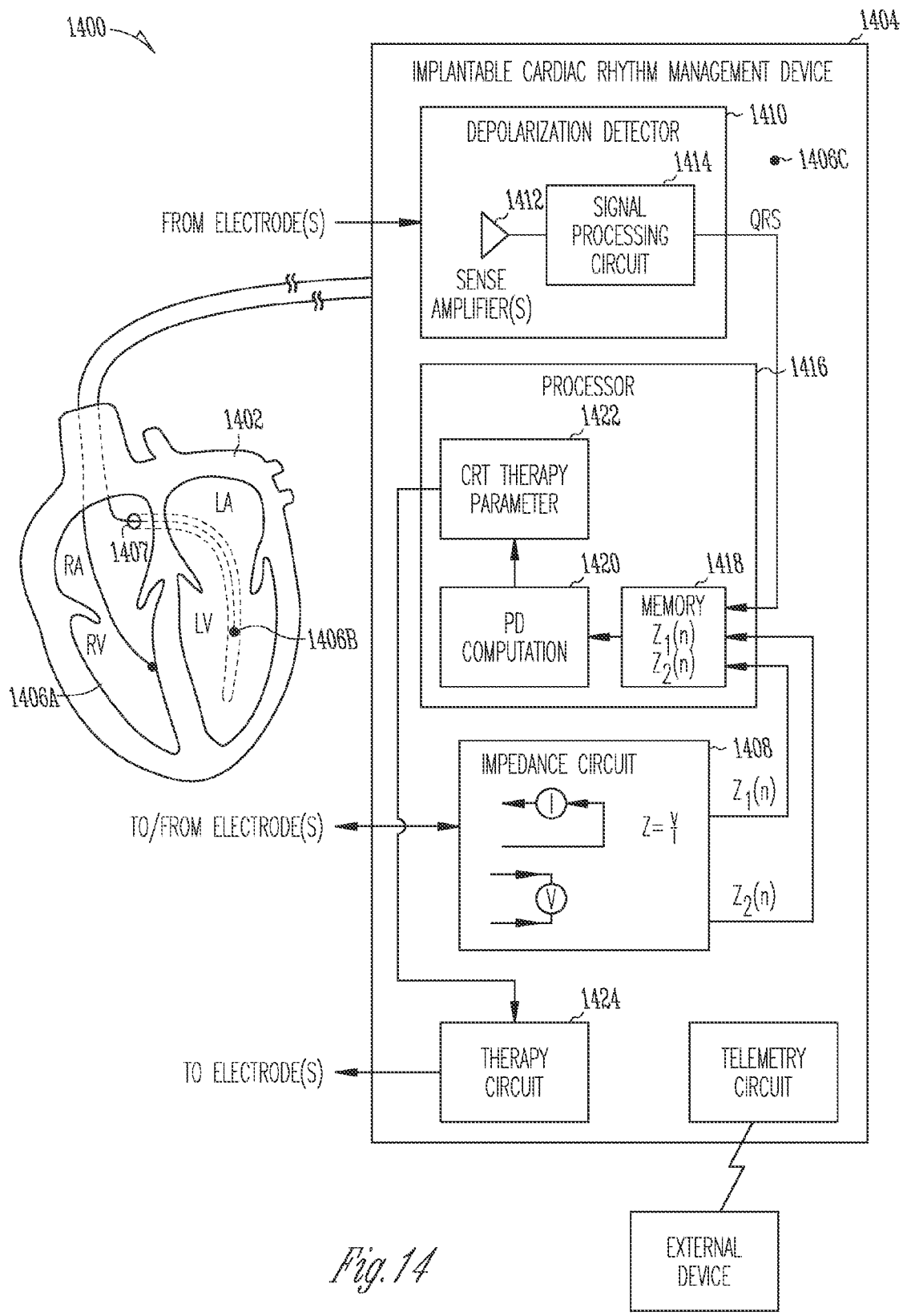
FIG. 14 is a schematic diagram illustrating generally one example of portions of a system and portions of an environment with which it is used.

FIG. 14 is a schematic diagram illustrating generally one example of portions of a system 1400 and portions of an environment with which it is used, including a heart 1402. In this example, the system 1400 includes an implantable cardiac function management device 1404. In one example, the device 1404 is coupled to the heart 1402 using one or more intravascular or other leads. The leads provide electrodes 1406 in association with the heart 1402. FIG. 14 illustrates an example that includes a first electrode 1406A that is located at or near a midportion of a right ventricular septum, a second electrode 1406B that is located in association with a left ventricular freewall, such as by being introduced on an intravascular lead that is inserted into coronary sinus 1407 toward a coronary sinus vein. A third electrode 1406C is located on a hermetically-sealed housing ("can") of the implantable device 1404 (or, alternatively, on an insulating "header" extending from the housing of the implantable device 1404).

In FIG. 14, the device 1404 includes an impedance circuit 1408 for measuring a first impedance between the first electrode 1406A and the third electrode 1406C and a second impedance between the second electrode 1406B and the third electrode 1406C. The first and second impedances are modulated as the septum and freewall portions of the left ventricle contract and expand. In one example, this impedance modulation is used to detect asynchrony between two different locations associated with the left ventricle, as discussed below.

In the example of FIG. 14, a depolarization detector circuit 1410 detects intrinsic electrical heart depolarizations, such as by using one or more sense amplifiers 1412 or signal processing circuits 1414 to detect QRS complexes, which are depolarizations corresponding to ventricular heart contractions. The time interval between two successive QRS complexes can be used to define a cardiac cycle. In one example, the impedance modulation is monitored over all or a particular desired portion of a cardiac cycle for making the asynchrony determination, as discussed below.

In the example of FIG. 14, a microprocessor, microcontroller, or other processor circuit 1416 executes instructions to provide computational ability. The impedance circuit 1408 provides a sampled data first ventricular impedance waveform $Z_1(n)$ and a sampled data second ventricular impedance waveform $Z_2(n)$ to the processor 1416 to be stored in a memory circuit 1418 located within or external to the processor 1416. In one example, the processor 1416 samples at least a portion of a cardiac cycle's worth of the first ventricular impedance waveform $Z_1(n)$ and of the second ventricular impedance waveform $Z_2(n)$ to compute an indication of the degree of asynchrony (or, conversely, of synchrony) between the first (e.g., septal) and second (e.g., freewall) portions of the left ventricle, as discussed below. In one example, this indication is provided by a phase difference (PD) computation module 1420 comprising instructions that are executed by the processor 1416. In a further example, the PD or other indication of asynchrony or synchrony is used to control at least one cardiac resynchronization therapy (CRT) parameter 1422. The CRT parameter 1422, in turn, controls one or more aspects of the delivery of stimulation pulses or other CRT therapy by therapy circuit 1424, which is coupled to electrodes associated with the heart 1402, such as electrodes 1406 or other electrodes.

Impedance measurement circuit 1408 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 1406A and 1406C, or the present electrodes 1406B and 1406C. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 1406A and 1406C, or between the present electrodes 1406B and 1406C. In one example, the signal processing circuit includes a preamplifier, demodulator, and bandpass filter for extracting the impedance data from the carrier signal, before conversion into digital form by an A/D converter. Further processing is performed digitally, and is performed differently in the present system 1400 than in the Hartley et al. U.S. Pat. No. 6,076,015. The impedance circuit 1408 of the present system typically includes a digital filter that passes frequency components of the measured impedance signal that are close to the frequency of heart contractions. The digital filter typically attenuates other lower or higher frequency components of the measured impedance signal.

Figure 15:
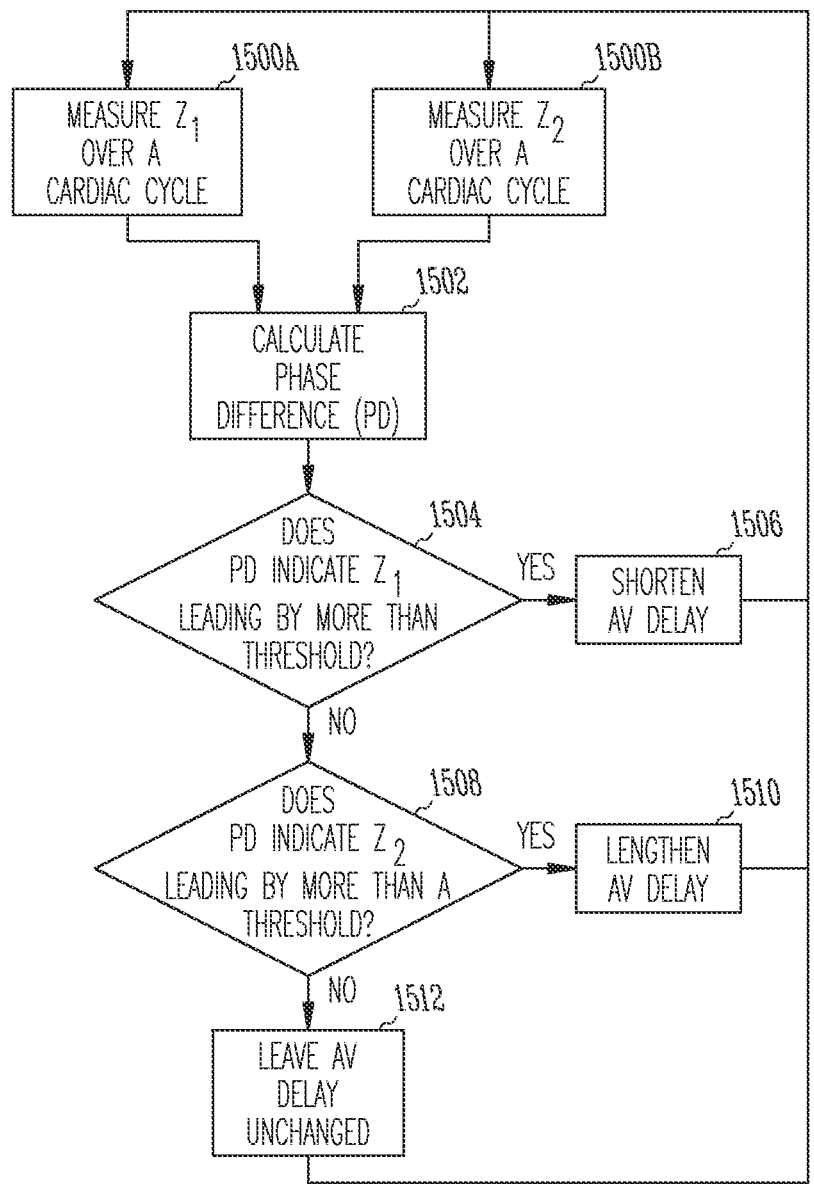
FIG. 15 is a flow chart illustrating generally one example of a technique for determining a degree of synchrony or asynchrony between septal and left ventricular freewall portions of a heart.

FIG. 15 is a flow chart illustrating generally one example of a technique for determining a degree of synchrony or asynchrony between first and second locations of left ventricular contractions of a heart. At 1500A, a first ventricular impedance ($Z_1$) is monitored over a cardiac cycle, such as by injecting a subthreshold (i.e., non-contraction-evoking) current (e.g., between electrodes 1406A and 1406C) and measuring a responsive voltage (e.g., using electrodes 1406A and 1406C). Concurrent with 1500A, at 1500B, a second ventricular impedance ($Z_2$) is monitored over the same cardiac cycle, such as by injecting a subthreshold current (e.g., between electrodes 1406B and 1406C) and measuring a responsive voltage (e.g., using electrodes 1406B and 1406C).

At 1502, a phase difference (PD) between the first and second locations of the ventricular contractions is calculated using $Z_1$ and $Z_2$. In one embodiment, the phase difference is calculated by measuring a time difference between the same artifact on each of the $Z_1$ and $Z_2$ signals. In one example, a zero-cross detector detects a like zero-crossing artifact in each of the $Z_1$ and $Z_2$ signals, and PD is then calculated as the time difference between occurrences of these two like zero-crossings. In another example, a peak-detector detects a like peak artifact in each of the $Z_1$ and $Z_2$ signals, and PD is then calculated as the time difference between occurrences of these two like peaks. In yet another example, a level-detector detects a like level in each of the $Z_1$ and $Z_2$ signals, and PD is then calculated as a time difference between the occurrences of these two like signal levels.

Figure 16:
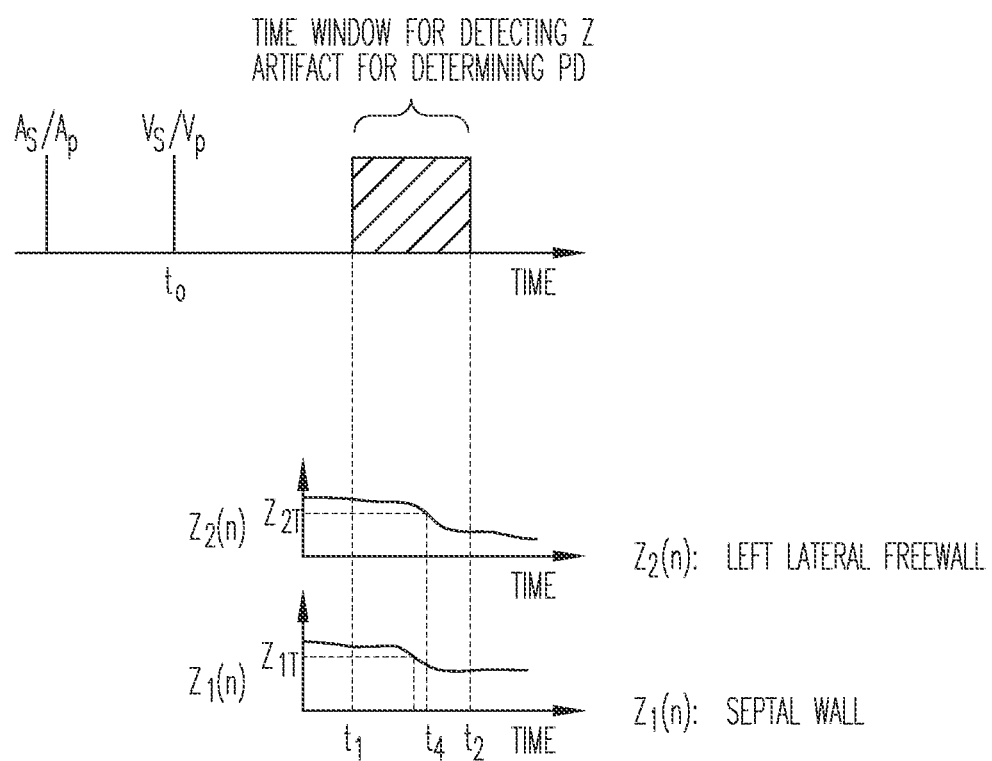
FIG. 16 is a conceptualized (not real data) signal diagram illustrating an embodiment in which a time window is established for identifying an impedance artifact.

In one embodiment, in order to better identify a like impedance artifact in each of the $Z_1$ and $Z_2$ signals for obtaining the phase difference, the zero-crossing, peak-detect, level-detect, etc. is performed during a particular time window portion of the cardiac cycle. In one example, this is accomplished by establishing such a time window relative to a QRS complex or other electrical artifact as detected by the depolarization detector 1410, as illustrated in the conceptualized (not real data) signal diagram of FIG. 16. In FIG. 16, a time window between $t_1$ and $t_2$ is triggered following predetermined delay from a ventricular sense ($V_S$) QRS complex or ventricular pace at time $t_0$. During the time window, the $Z_1$ and $Z_2$ signals are examined for the occurrence of a particular impedance artifact. In the illustrated conceptual example, the impedance artifact is an $Z_2$ falling below a certain threshold value $Z_{2T}$ (which occurs, in this example, at time $t_4$) and a corresponding $Z_1$ falling below a corresponding threshold value $Z_{1T}$ (which occurs, in this example, at time $t_3$). In this example, the PD magnitude is $t_4-t_3$ with $Z_1$ (septum) leading $Z_2$ (LV freewall).

In FIG. 15, at 1504 if PD indicates that $Z_1$ (the septum) is leading $Z_2$ (the left ventricular freewall) by more than a threshold value (PDT+), then at 1506, the AV delay is shortened by a small incremental value, which tends to reduce the amount by which the septum leads the left ventricular freewall. Otherwise, at 1508, if the PD indicates that $Z_2$ (the left ventricular freewall) is leading $Z_1$ (the septum) by more than a threshold value (PDT−), then at 1510, the AV delay is lengthened by a small incremental value, which tends to reduce the amount by which the left ventricular freewall leads the septum. Otherwise, at 1512, if neither $Z_1$ (septum) or $Z_2$ (left ventricular freewall) is leading by more than its respective threshold, then the AV delay is left unchanged, which tends to leave the synchrony between the septum and the left ventricular freewall unchanged. The behavior of 1504-1512 is further understood by reference to the phase delay vs. AV delay graph of FIG. 17. Using PD as an error signal in a closed loop system to control a CRT parameter (such as AV Delay), FIG. 17 illustrates how synchrony between the septum and left ventricular freewall is promoted.

Figure 17:
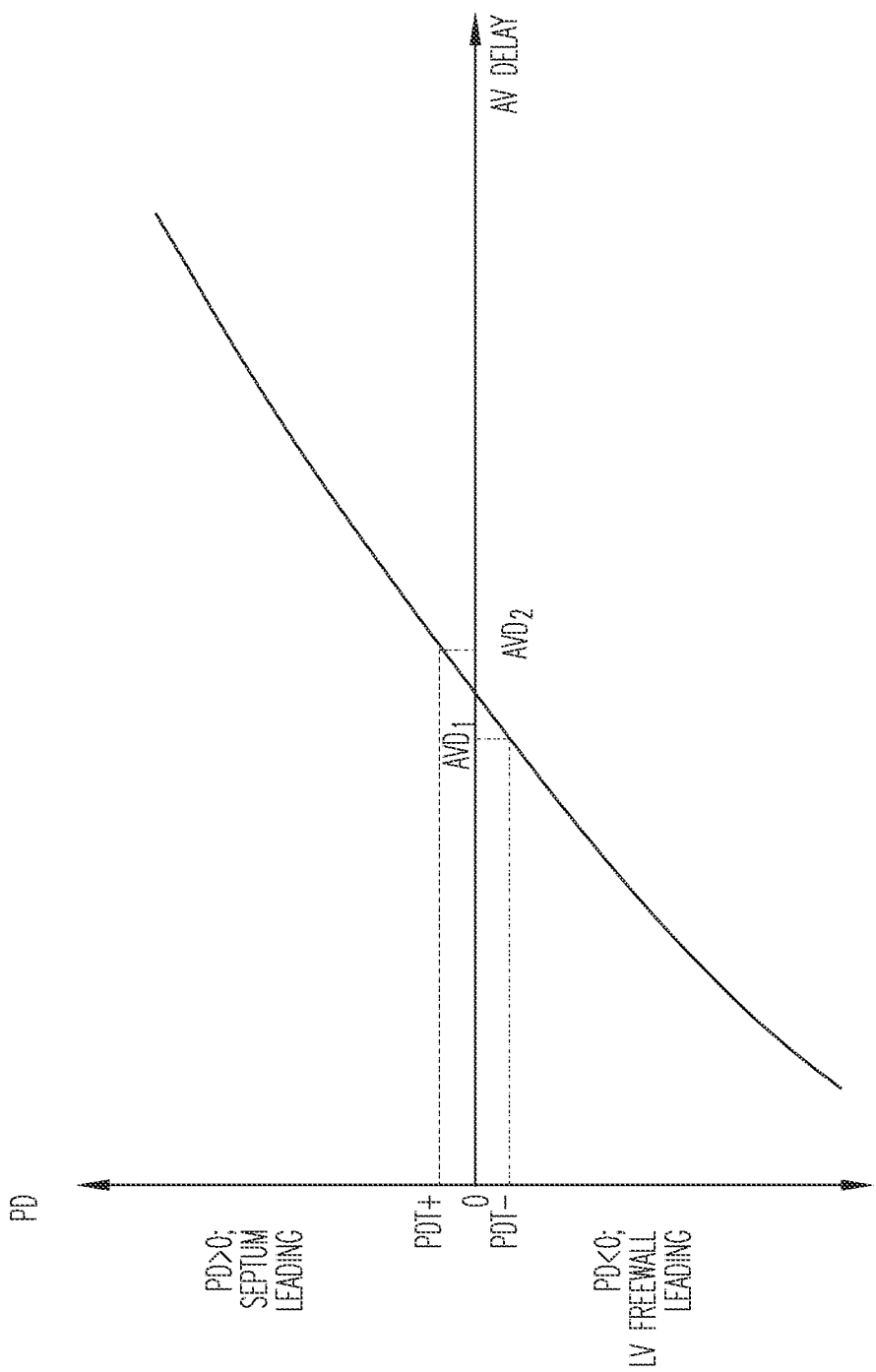
FIG. 17 is a graph of phase delay vs. AV delay.

Although FIGS. 15 and 17 illustrate AV delay as the particular CRT parameter being modified to effect closed-loop control reducing PD, other CRT parameters could similarly be modified to reduce PD. Another example of a CRT parameter is LV offset (LVO), which is the difference between a right ventricular AV delay (AVDR) and a left ventricular AV delay (AVDL). More particularly, LVO=AVDL−AVDR. Therefore, a positive LVO indicates that the right ventricle is programmed to be stimulated earlier than the left ventricle; a negative LVO indicates that the left ventricle is programmed be stimulated earlier than the right ventricle. In one example, the LVO is adjusted in a closed-loop fashion to reduce the PD error signal between the septum and the left ventricular freewall, in a similar manner to that illustrated in FIGS. 15 and 17. Similarly, other CRT parameter(s) can be adjusted in a closed-loop fashion to reduce the PD error signal and improve right and left ventricular mechanical synchrony.

The example described above with respect to FIGS. 14-17 reduces the PD by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may reduce the PD at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Example 5

Figure 18:
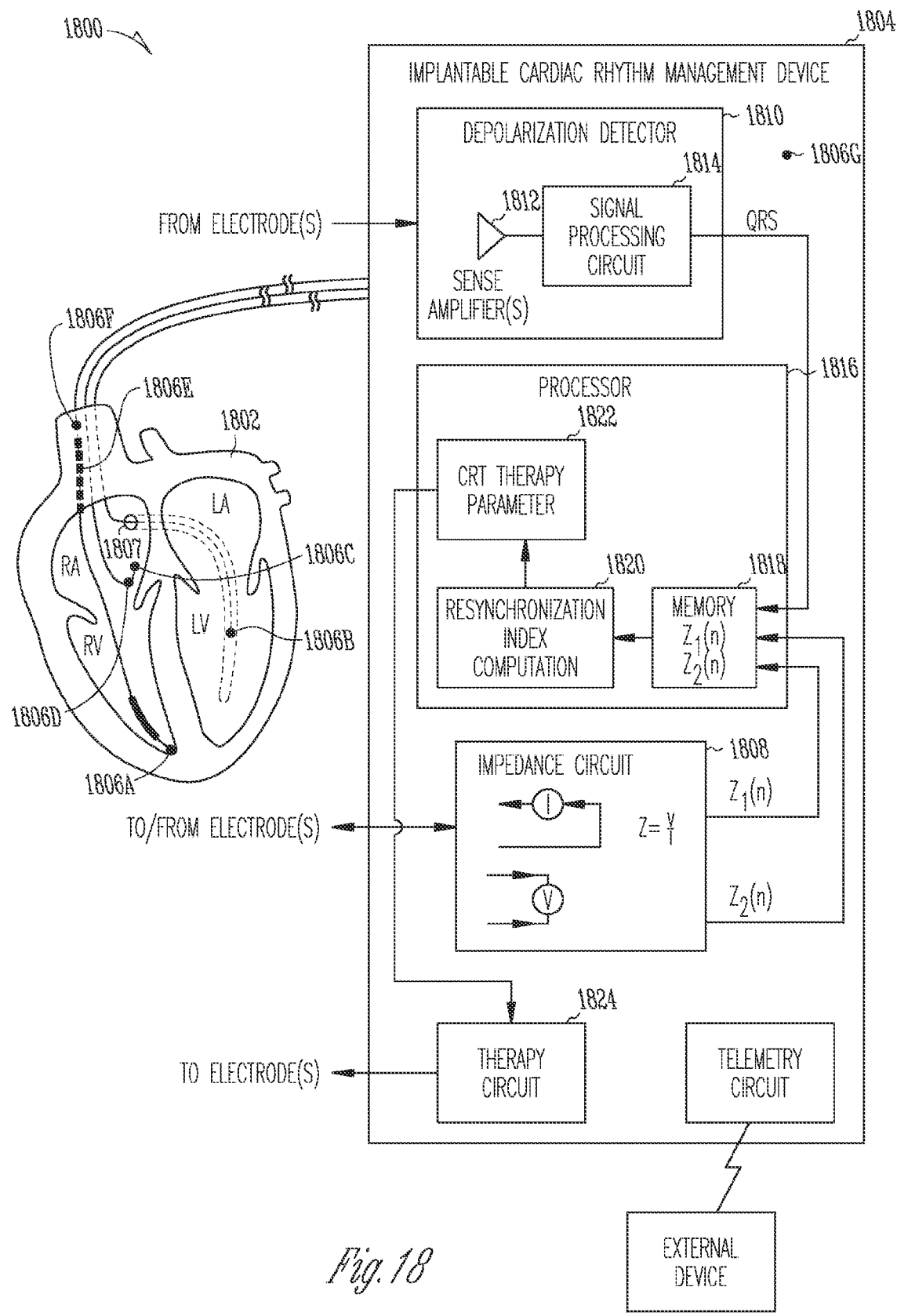
FIG. 18 is a schematic diagram illustrating generally one example of portions of a system and portions of an environment with which it is used.

FIG. 18 is a schematic diagram illustrating generally one example of portions of a system 1800 and portions of an environment with which it is used, including a heart 1802. In this example, the system 1800 includes an implantable cardiac function management device 1804. In one example, the device 1804 is coupled to the heart 1802 using one or more intravascular or other leads. The leads provide electrodes 1806 in association with the heart 1802. FIG. 18 illustrates an example that includes at least seven electrodes selectable for impedance measurement. A first electrode 1806A is located at or near a middle or apical portion of the right ventricle, such as by being introduced on an intravascular lead that is inserted into the right ventricle through the superior vena cava and the right atrium. A second electrode 1806B is located in association with a left ventricular freewall, such as by being introduced on an intravascular lead that is inserted into coronary sinus 1807 toward a lateral or posterior coronary sinus vein. A third electrode 1806C and a fourth electrode 1806D are located in the right atrium near the atrial septum or the appendage, such as by being introduced on an intravascular lead that is inserted into the right atrium through the superior vena cava. A fifth electrode 1806E and a six electrode 1806F are located in the superior vena cava, such as by being introduced on the intravascular lead that also includes the electrode 1806A. In one example, as illustrated in FIG. 18, the first electrode 1806A is a right ventricular tip electrode of a pacing-defibrillation lead. The second electrode 1806B is a left ventricular tip electrode of a coronary sinus pacing lead. The third electrode 1806C is a right atrial tip electrode of a right atrial pacing lead. The fourth electrode 1806D is a right atrial ring electrode of the right atrial pacing lead. The fifth electrode 1806E is a superior vena cava coil electrode of the pacing-defibrillation lead. The sixth electrode 1806F is superior vena cava ring electrode of the pacing-defibrillation lead. Another electrode 1806G is located on a hermetically-sealed housing ("can") of the implantable device 1804 (or, alternatively, on an insulating "header" extending from the housing of the implantable device 1804).

In FIG. 18, the device 1804 includes an impedance circuit 1808. In one example, impedance circuit 1808 measures a right ventricular impedance between (i) the first electrode 1806A and (ii) one of the third electrode 1806C and the fourth electrode 1806D and a left ventricular impedance between (i) the second electrode 1806B and (ii) one of the third electrode 1806C and the fourth electrode 1806D. In another example, impedance circuit 1808 measures a right ventricular impedance between (i) the first electrode 1806A and (ii) one of the fifth electrode 1806E and the sixth electrode 1806F and a left ventricular impedance between (i) the second electrode 1806B and (ii) one of the fifth electrode 1806E and the sixth electrode 1806F. The right and left ventricular impedances are modulated as the right and left ventricles contract and expand. In one example, this impedance modulation is used to detect asynchrony between the left and right ventricular heart contractions, as discussed below.

In the example of FIG. 18, the device 1804 includes a depolarization detector circuit 1810 that detects intrinsic electrical heart depolarizations, such as by using one or more sense amplifiers 1812 or signal processing circuits 1814 to detect QRS complexes, which indicate ventricular depolarizations corresponding to ventricular heart contractions. The time interval between two successive QRS complexes can be used to define a cardiac cycle. In one example, relative timing between impedance modulation and the ventricular depolarizations is to detect asynchrony between the left and right ventricular heart contractions, as discussed below.

In the example of FIG. 18, a microprocessor, microcontroller, or other processor circuit 1816 executes instructions to provide computational ability. The impedance circuit 1808 provides a sampled data right ventricular impedance waveform $Z_1(n)$, a sampled data left ventricular impedance waveform $Z_2(n)$, and a sampled data representation of detected intrinsic electrical heart depolarizations to the processor 1816 to be stored in a memory circuit 1818 located within or external to the processor 1816. In one example, the processor 1816 samples at least a portion of a cardiac cycle's worth of the right ventricular impedance waveform $Z_1(n)$, the left ventricular impedance waveform $Z_2(n)$, and right and left ventricular depolarizations to compute an indication of the degree of asynchrony (or, conversely, of synchrony) between the right and left ventricles, as discussed below. In one example, this indication is provided by one or more resynchronization index parameters such as a time interval between peak maximum right ventricular impedance ($RVZ_{max}$) and peak maximum right ventricular LV impedance ($LVZ_{max}$), the difference between slopes of the right ventricular impedance waveform and the left ventricular impedance waveform each measured at a certain point, the difference between the interval between the right ventricular depolarization and the peak maximum right ventricular impedance and the interval between the left ventricular depolarization and the peak maximum left ventricular impedance, and the time interval between the right ventricular depolarization and the left ventricular depolarization. In one example, such one or more resynchronization index parameters are produced by a resynchronization index computation module 1820 including instructions that are executable by the processor 1816. In one example, the one or more resynchronization index parameters provide for indications of efficacy of cardiac resynchronization therapy (CRT) for each individual potential patient and provide for verifications of efficacy of CRT for each individual patient having been receiving CRT. In a further example, the one or more resynchronization index parameters are used to control at least one cardiac resynchronization therapy (CRT) parameter 1822. The CRT parameter 1822, in turn, controls one or more aspects of the delivery of stimulation pulses or other CRT therapy by therapy circuit 1824, which is coupled to electrodes associated with the heart 1802, such as electrodes 1806 or other electrodes.

Impedance measurement circuit 1808 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 1806A and 1806C, or the present electrodes 1806B and 1806D. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 1806A and 1806C, or between the present electrodes 1806B and 1806D. In one example, the signal processing circuit includes a preamplifier, demodulator, and bandpass filter for extracting the impedance data from the carrier signal, before conversion into digital form by an A/D converter. Further processing is performed digitally, and is performed differently in the present system 1800 than in the Hartley et al. U.S. Pat. No. 6,076,015. The impedance circuit 1808 of the present system typically includes a digital filter that passes frequency components of the measured impedance signal that are close to the frequency of heart contractions. The digital filter typically attenuates other lower or higher frequency components of the measured impedance signal.

Figure 19:
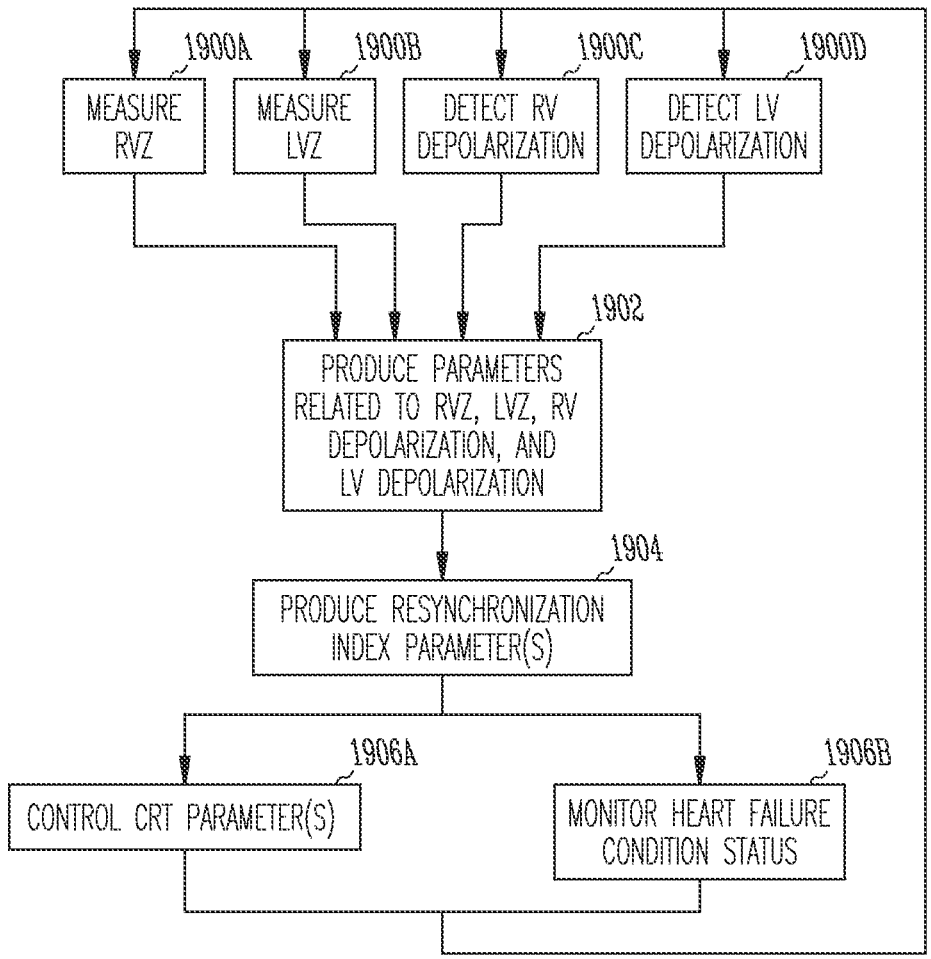
FIG. 19 is a flow chart illustrating generally one example of a technique for determining resynchronization index parameters each indicative of a degree of synchrony or asynchrony between left and right ventricular contractions of a heart.

FIG. 19 is a flow chart illustrating generally one example of a technique for determining one or more resynchronization index parameters each indicative of a degree of synchrony or asynchrony between left and right ventricular contractions of a heart. At 1900A, a right ventricular impedance (RVZ) is measured over a cardiac cycle, such as by injecting a subthreshold (i.e., non-contraction-evoking) current (e.g., between electrodes 1806A and 1806C) and measuring a responsive voltage (e.g., using electrodes 1806A and 1806C). Concurrent with 1900A, at 1900B, a left ventricular impedance (LVZ) is measured over the same cardiac cycle, such as by injecting a subthreshold current (e.g., between electrodes 1806B and 1806D) and measuring a responsive voltage (e.g., using electrodes 1806B and 1806D). Concurrent with 1900A and 1900B, at 1900C, a right ventricular depolarization is detected over the same cardiac cycle, such as by sensing a right ventricular electrogram (e.g., using electrodes 1806A and 1806G) and detecting a QRS complex from the right ventricular electrogram. Concurrent with 1900A, 1900B, and 1900C, at 1900D, a left ventricular depolarization is detected over the same cardiac cycle, such as by sensing a left ventricular electrogram (e.g., using electrodes 1806B and 1806G) and detecting a QRS complex from the left ventricular electrogram.

Figure 20:
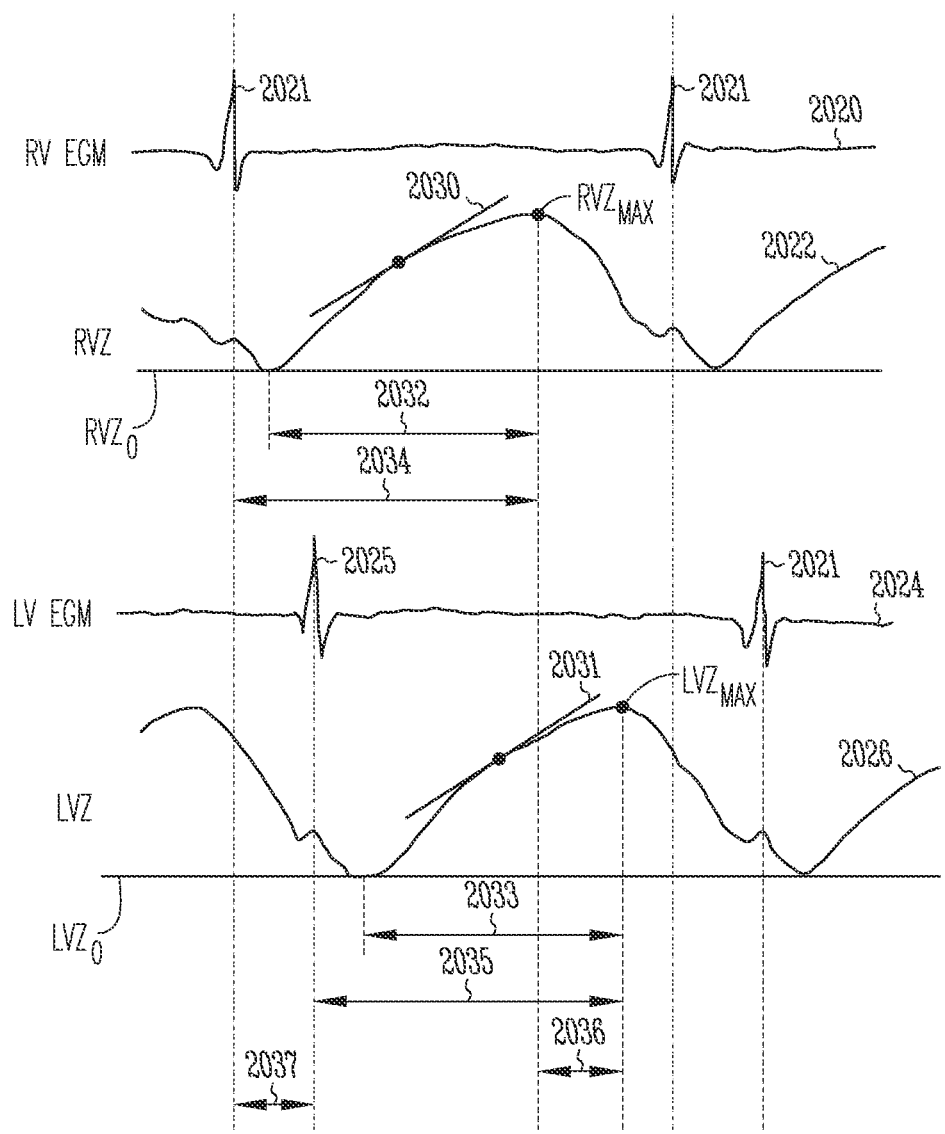
FIG. 20 is a conceptualized (not real data) signal diagram illustrating an embodiment in which various parameters are measured from electrograms and impedance signals.

At 1902, parameters related to the right ventricular impedance (RVZ), the left ventricular impedance (LVZ), the right ventricular depolarization, and the left ventricular depolarization are produced. This includes determination of one or both of a value and the time at which the value occurs. These parameters are illustrated in the conceptualized (not real data) signal diagram of FIG. 20. FIG. 20 illustrates a right ventricular electrogram (RV EGM) 2020 indicative of right ventricular depolarizations 2021, a right ventricular impedance waveform (RVZ) 2022, a left ventricular electrogram (LV EGM) 2024 indicative of left ventricular depolarizations 2025, and a left ventricular impedance waveform (LVZ) 2026. $RVZ_0$ is the baseline impedance value of the right ventricular impedance. $LVZ_0$ is the baseline impedance value of the left ventricular impedance. The baseline impedance values vary with a patient's heart size and depend on myocardial mass and blood volume. In one example, each baseline impedance value is established at time of implant. In yet another example, each baseline impedance value is established while a patient is in a predetermined physiologic state, such as at rest. In some examples, the baseline impedance value is established by forming an ensemble or other average or central tendency of minimum values of the impedance waveform. $RVZ_{max}$ is the maximum peak impedance value of the right ventricular impedance. $LVZ_{max}$ is the maximum peak impedance value of the left ventricular impedance. The maximum peak impedance value provides a measure of, among other things, the maximum change in size of a heart due to changing blood volume. Another parameter providing for a measure of the volume of blood flowing through the heart is the area between the impedance waveform and the baseline impedance value. $RVZ_{area}$ is the area between the waveform 2022 and $RVZ_0$. $LVZ_{area}$ is the area between the waveform 2026 and $LVZ_0$. This area provides an approximation of the integral of the intracardiac impedance over the cardiac cycle. The time interval of maximum right ventricular impedance change 2032, $RVT_{Z0-Zmax}$, is measured between the baseline point and the peak of waveform 2022 over a cardiac cycle. The baseline point of the waveform 2022 is the time when the waveform 2022 rises across the $RVZ_0$. The peak of the waveform 2022 is the time when waveform 2022 reaches the $RVZ_{max}$. The time interval of maximum left ventricular impedance change 2033, $LVT_{Z0-Zmax}$, is measured between the baseline point and the peak of waveform 2026 over the cardiac cycle. The baseline point of the waveform 2026 is the time when the waveform 2026 rises across the $LVZ_0$. The peak of the waveform 2026 is the time when waveform 2026 reaches the $LVZ_{max}$. The time interval of maximum ventricular impedance change provides for a measure of heart contraction speed. A slope of the waveform 2022, $RVS_Z$, is measured at a predetermined point between the baseline point and the peak of the waveform 2022. A slope of the waveform 2026, $LVS_Z$, is measured at a predetermined point between the baseline point and the peak of the waveform 2026. The slope of the impedance waveform provides for a measure of the efficiency of heart contractions. One specific example of such slopes is illustrated in FIG. 20 as slopes 2030 and 2031. The slope 2030 of the waveform 2022, $RVS_{1/2Z0-Zmax}$, is measured at the midpoint between the baseline point and the peak of the waveform 2022. The slope 2031 of the waveform 2026, $LVS_{1/2TZ0-Zmax}$, is measured at the midpoint between the baseline point and the peak of the waveform 2026. In another example, a slope of the waveform 2022, $RVS_{80\%TZ0-Zmax}$, is measured at the end of an interval that starts with the baseline point and is 80% of the time interval between the baseline point and the peak of the waveform 2022. A slope of the waveform 2026, $LVS_{80\%TZ0-Zmax}$, is measured at the end of an interval that starts with the baseline point and is 80% of the time interval between the baseline point and the peak of the waveform 2026.

A time interval 2034, $RVT_{V-Zmax}$, is measured between the time when the right ventricular depolarization 2021 occurs and the peak of the waveform 2022 over a cardiac cycle. A time interval 2035, $LVT_{V-Zmax}$, is measured between the time when the left ventricular depolarization 2025 occurs and the peak the waveform 2026 over the cardiac cycle. The time intervals 2034 and 2035 each provide for a measure of electromechanical association for one of the right and left ventricles.

At 1904, one or more resynchronization index parameters are produced using the parameters produced at 1902. One example of a resynchronization index parameter indicative of mechanical synchrony between the right and left ventricular contractions is a time interval 2036 between the peak of the waveform 2022 and the peak of the waveform 2026 during a cardiac cycle, $T_{RVZmax-LVZmax}$. Another example of a resynchronization index parameter indicative of mechanical synchrony between the right and left ventricular contractions is the difference between the slope $RVS_Z$ and the slope $LVS_Z$ during a cardiac cycle, $\Delta S_Z$. Specific examples of the $\Delta S_Z$ includes $\Delta S_{1/2TZ0-Zmax}$ (the difference between the slope 2030 ($RVS_{1/2TZ0-Zmax}$) and the slope 2031 ($LVS_{1/2TZ0-Zmax}$) during a cardiac cycle) and $\Delta S_{80\%TZ0-Zmax}$ (the difference between the slope $RVS_{80\%TZ0-Zmax}$ and the slope $LVS_{80\%TZ0-Zmax}$ during a cardiac cycle). Another example of a resynchronization index parameter indicative of mechanical synchrony between the right and left ventricular contractions is the difference between the interval 2034 ($RVT_{V-Zmax}$) and the interval 2035 ($LVT_{V-Zmax}$) during a cardiac cycle, $\Delta T_{V-Zmax}$. An example of a resynchronization index parameter indicative of electrical synchrony between the right and left ventricular contractions is the interventricular interval 2037 between the right ventricular depolarization 2021 and the left ventricular depolarization 2025 during a cardiac cycle, $T_{RV-LV}$.

At 1906A, one or more of the resynchronization index parameters are used to control one or more CRT parameters. Examples of such CRT parameters include AV delay and interventricular offset, such as a right ventricular AV delay and an LV offset (LVO). The one or more CRT parameters are adjusted to reduce the degree of ventricular asynchrony as measured by the one or more resynchronization index parameters. In one example, an automatic CRT parameter optimization algorithm is executed to optimize one or more CRT parameters using automatically measured one or more resynchronization index parameters. For example, pacing pulses are delivered using a plurality of AV delays, one at a time, and the value of a resynchronization index parameter is produced for each of the AV delays. The value of the AV delay associated with the value of the resynchronization index parameter corresponding to the minimum degree of ventricular asynchrony is selected as the optimal AV delay for the CRT. In another example, a physician or other caregiver adjusts one or more CRT parameters using automatically or manually measured one or more resynchronization index parameters. For example, the physician or other caregiver programs a plurality of AV delays, one at a time, and measures the value of a resynchronization index parameter produced for each of the AV delays. The value of the AV delay associated with the value of the resynchronization index parameter corresponding to the minimum degree of ventricular asynchrony is selected as the optimal AV delay for the CRT. In another example, a closed loop system is used to dynamically adjust or optimize one or more CRT parameters using one or more resynchronization index parameters as input signals.

In addition to 1906A, or instead of 1906A, at 1906B, the one or more resynchronization index parameters are monitored as an indication of a patient's heart failure condition status. In one example, the one or more resynchronization index parameters are produced for a patient for predicting efficacy of CRT for the patient. Generally, patients showing higher degrees of ventricular asynchrony are more likely to respond to CRT. In another example, one or more resynchronization index parameters are monitored as an indication of efficacy of CRT. The CRT is considered effective on a patient if the patient's degree of ventricular asynchrony is reduced in response to the CRT.

CONCLUSION

Portions of the above description have emphasized using LVZ to determine the control parameter. This is because, in most CHF patients, enlargement occurs in the left ventricle, and therefore, cardiac resynchronization therapy is most effective when used to help control left ventricular cardiac output. However, in some patients, enlargement occurs in the right ventricle instead of the left ventricle. For such patients, the cardiac resynchronization techniques described above can be applied analogously to the right ventricle, or to both ventricles.

At least some of the examples described above with improve the stroke volume of a ventricle by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may improve the stroke volume at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Although the above examples have emphasized beat-by-beat closed-loop control of CRT parameters, it is understood that such techniques are also applicable to providing useful information to a physician or other caregiver to help guide the appropriate programming of one or more CRT parameters.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the present document, including in the following claims, the terms "first," "second," and "third," etc. are used merely as labels, and are not intended to impose numerical requirements on their objects.

What is claimed is:

1. A system for monitoring a heart having first and second ventricles, the system comprising:
   a device including:
      an impedance measurement circuit, including terminals configured to be coupled to electrodes in association with the first ventricle to measure a first impedance signal that is substantially indicative of a volume of the first ventricle as the first ventricle expands and contracts during a cardiac cycle of the heart and in association with the second ventricle to measure a second impedance signal that is substantially indicative of a volume of the second ventricle as the second ventricle expands and contracts during the cardiac cycle; and
      a processor, coupled to the impedance measurement circuit to receive information about the first and second impedance signals over the cardiac cycle, the processor configured to perform instructions to detect a first peak of the first impedance signal during the cardiac cycle, detect a second peak of the second impedance signal during the cardiac cycle, determine a first type point on the first impedance signal, the first type point being a function of the first peak, determine a second type point on the second impedance signal, the second type point being a function of the second peak, compute a first slope of the first impedance signal at the first type point on the first impedance signal, compute a second slope of the second impedance signal at the second type point on the second impedance signal, and produce a first resynchronization parameter using a difference between the first slope and the second slope, the first resynchronization parameter indicative of a degree of cardiac mechanical synchrony or asynchrony between the first and second ventricles.

2. The system of claim 1, in which the device includes an implantable medical device.

3. The system of claim 2, in which the implantable medical device includes a telemetry circuit, coupled to the processor, to receive information about the degree of synchrony or asynchrony, the telemetry circuit configured to communicate data associated with the information about the degree of synchrony or asynchrony from the implantable medical device.

4. The system of claim 2, in which the implantable medical device further includes a therapy circuit configured to provide a cardiac resynchronization therapy, and the processor is configured to perform instructions to adjust delivery of the cardiac resynchronization therapy using the first resynchronization parameter.

5. The system of claim 4, in which the processor is configured to perform instructions to adjust one or more cardiac resynchronization therapy parameters including an atrioventricular delay to reduce the degree of cardiac mechanical asynchrony as indicated by the first resynchronization parameter.

6. The system of claim 1, in which the processor is configured to perform instructions to detect a first baseline point of the first impedance signal during the cardiac cycle, detect a second baseline point of the second impedance signal during the cardiac cycle, locate the first type point between the first baseline point and the first peak, and locate the second type point between the second baseline point and the second peak, the first peak being a first point at which the first impedance signal reaches a first maximum value, the second peak being a second point at which the second impedance signal reaches a second maximum value, the first baseline point being a point at which the first impedance signal rises across a first baseline impedance, the second baseline point being a point at which the second impedance signal rises across a second baseline impedance.

7. The system of claim 6, in which the processor is configured to perform instructions to locate a first midpoint between the first baseline point and the first peak, the first midpoint being the first type point, and locate a second midpoint between the second baseline point and the second peak, the second midpoint being the second type point.

8. The system of claim 6, in which the processor is configured to perform instructions to locate an end of a first time interval that starts with the first baseline point and is 80% of a time interval between the first baseline point and the first peak, the end of the first time interval being the first type point, and locate an end of a second time interval that starts with the second baseline point and is 80% of a time interval between the second baseline point and the second peak, the end of the second time interval being the second type point.

9. The system of claim 6, in which the processor is configured to perform instructions to establish the first baseline impedance by forming an average or central tendency of minimum values of the first impedance signal, and establish the second baseline impedance by forming an average or central tendency of minimum values of the second impedance signal.

10. The system of claim 1, in which the device further includes a depolarization detector to detect a first ventricular depolarization of the first ventricle and a second ventricular depolarization of the second ventricle during the cardiac cycle, and the processor is configured to perform instructions to produce a second resynchronization parameter indicative of a degree of cardiac electrical synchrony or asynchrony between the right and left ventricles by computing an interventricular interval between a time interval between the first ventricular depolarization and the second ventricular depolarization.

11. A system for monitoring a heart having first and second ventricles, the system comprising:
a device comprising:
an impedance measurement circuit, including terminals configured to be coupled to electrodes in association with the first ventricle to measure a first impedance signal that is substantially indicative of a volume of the first ventricle as the first ventricle expands and contracts during a cardiac cycle of the heart and in association with the second ventricle to measure a second impedance signal that is substantially indicative of a volume of the second ventricle as the second ventricle expands and contracts during the cardiac cycle;
a depolarization detector to detect a first ventricular depolarization of the first ventricle and a second ventricular depolarization of the second ventricle during the cardiac cycle; and
a processor, coupled to the impedance measurement circuit to receive information about the first and second impedance signals over the cardiac cycle, the processor configured to perform instructions to detect a first peak of the first impedance signal during the cardiac cycle, detect a second peak of the second impedance signal during the cardiac cycle, measure a first time interval between the first ventricular depolarization and the first peak, measure a second time interval between the second ventricular depolarization and the second peak, and produce a first resynchronization parameter using a difference between the first time interval and the second time interval, the first peak being a first point at which the first impedance signal reaches a first maximum value, the second peak being a second point at which the second impedance signal reaches a second maximum value, the first resynchronization parameter indicative of a degree of cardiac mechanical synchrony or asynchrony between the first and second ventricles.

12. The system of claim 11, in which the device includes an implantable medical device.

13. The system of claim 12, in which the implantable medical device includes a telemetry circuit, coupled to the processor, to receive information about the degree of synchrony or asynchrony, the telemetry circuit configured to communicate data associated with the information about the degree of synchrony or asynchrony from the implantable medical device.

14. The system of claim 12, in which the implantable medical device further includes a therapy circuit configured to provide a cardiac resynchronization therapy, and the processor is configured to perform instructions to adjust delivery of the cardiac resynchronization therapy using the first resynchronization parameter.

15. The system of claim 14, in which the processor is configured to perform instructions to adjust one or more cardiac resynchronization therapy parameters including an atrioventricular delay to reduce the degree of cardiac mechanical asynchrony as indicated by the first resynchronization parameter.

16. The system of claim 11, in which the processor is configured to perform instructions to detect a first baseline point of the first impedance signal during the cardiac cycle, detect a second baseline point of the second impedance signal during the cardiac cycle, locate the first type point between the first baseline point and the first peak, and locate the second type point between the second baseline point and the second peak, the first baseline point being a point at which the first impedance signal rises across a first baseline impedance, the second baseline point being a point at which the second impedance signal rises across a second baseline impedance.

17. The system of claim 16, in which the processor is configured to perform instructions to locate a first midpoint between the first baseline point and the first peak, the first midpoint being the first type point, and locate a second midpoint between the second baseline point and the second peak, the second midpoint being the second type point.

18. The system of claim 16, in which the processor is configured to perform instructions to locate an end of a first time interval that starts with the first baseline point and is 80% of a time interval between the first baseline point and the first peak, the end of the first time interval being the first type point, and locate an end of a second time interval that starts with the second baseline point and is 80% of a time interval between the second baseline point and the second peak, the end of the second time interval being the second type point.

19. The system of claim 16, in which the processor is configured to perform instructions to establish the first baseline impedance by forming an average or central tendency of minimum values of the first impedance signal, and establish the second baseline impedance by forming an average or central tendency of minimum values of the second impedance signal.

20. The system of claim 11, in which the device further includes a depolarization detector to detect a first ventricular depolarization of the first ventricle and a second ventricular depolarization of the second ventricle during the cardiac cycle, and the processor is configured to perform instructions to produce a second resynchronization parameter indicative of a degree of cardiac electrical synchrony or asynchrony between the right and left ventricles by computing an interventricular interval between a time interval between the first ventricular depolarization and the second ventricular depolarization.

* * * * *